(12) United States Patent
Sagara et al.

(10) Patent No.: US 9,793,492 B2
(45) Date of Patent: Oct. 17, 2017

(54) COMPOUND, LIGHT EMITTER, AND ORGANIC LIGHT EMITTING DEVICE

(71) Applicants: KYUSHU UNIVERSITY NATIONAL UNIVERSITY CORPORATION, Fukuoka-shi, Fukuoka (JP); NIPPON STEEL & SUMIKIN CHEMICAL CO., LTD., Tokyo (JP)

(72) Inventors: Yuta Sagara, Fukuoka (JP); Hiroyuki Tanaka, Fukuoka (JP); Katsuyuki Shizu, Fukuoka (JP); Hiroshi Miyazaki, Kitakyushu (JP); Chihaya Adachi, Fukuoka (JP)

(73) Assignees: KYUSHU UNIVERSITY NATIONAL UNIVERSITY CORPORATION, Fukuoka (JP); NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 122 days.

(21) Appl. No.: 14/768,507

(22) PCT Filed: Feb. 14, 2014

(86) PCT No.: PCT/JP2014/053477
§ 371 (c)(1),
(2) Date: Aug. 18, 2015

(87) PCT Pub. No.: WO2014/126200
PCT Pub. Date: Aug. 21, 2014

(65) Prior Publication Data
US 2016/0005978 A1 Jan. 7, 2016

(30) Foreign Application Priority Data
Feb. 18, 2013 (JP) .................. 2013-028792

(51) Int. Cl.
*H01L 51/00* (2006.01)
*C09K 11/06* (2006.01)
(Continued)

(52) U.S. Cl.
CPC ........ *H01L 51/0071* (2013.01); *C07D 498/04* (2013.01); *C07D 513/04* (2013.01);
(Continued)

(58) Field of Classification Search
None
See application file for complete search history.

(56) References Cited

U.S. PATENT DOCUMENTS

| 2,807,622 A | 9/1957 | Theodor et al. |
| 2009/0108733 A1 | 4/2009 | Chin et al. |

FOREIGN PATENT DOCUMENTS

| CN | 101208405 A | 6/2008 |
| JP | H10340786 A | 12/1998 |

(Continued)

OTHER PUBLICATIONS

Yin-Hung et al., "Synthesis and Photophysical Properties of Some Benzoxazole and Benzothiazole Compounds", Macromolecules, 29(8) 2783-2795 (1996).
(Continued)

*Primary Examiner* — J. L. Yang
(74) *Attorney, Agent, or Firm* — Browdy and Neimark, P.L.L.C.

(57) ABSTRACT

A compound represented by D-A-D is useful as a light emitter for an organic electroluminescent device:

(Continued)

-continued

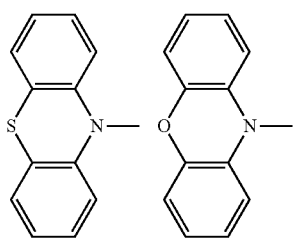

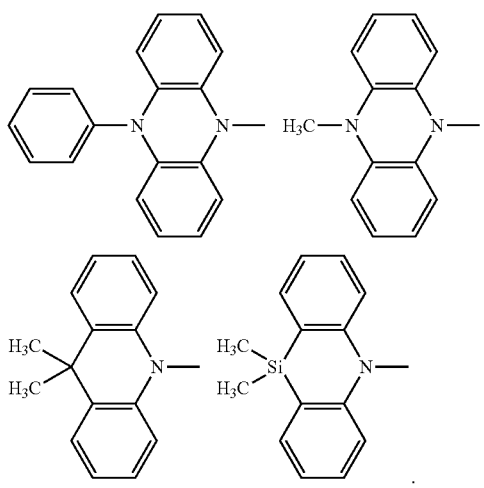

(51) Int. Cl.
*C07D 513/04* (2006.01)
*C07D 498/04* (2006.01)
*H01L 51/50* (2006.01)

(52) U.S. Cl.
CPC .......... *C09K 11/06* (2013.01); *H01L 51/0072* (2013.01); *C09K 2211/104* (2013.01); *C09K 2211/1007* (2013.01); *C09K 2211/1033* (2013.01); *C09K 2211/1037* (2013.01); *C09K 2211/1044* (2013.01); *H01L 51/006* (2013.01); *H01L 51/5012* (2013.01)

(56) References Cited

FOREIGN PATENT DOCUMENTS

| | | |
|---|---|---|
| JP | H11116579 A | 4/1999 |
| JP | 200582703 A | 3/2005 |
| JP | 2008546762 A | 12/2008 |
| WO | 2004/094389 | 11/2004 |
| WO | 2006137640 A1 | 12/2006 |

OTHER PUBLICATIONS

International Search Report, dated Mar. 18, 2014, in corresponding application No. JP2014053477.
International Preliminary Report, dated Feb. 14, 2014, in corresponding application No. JP2014053477.
Chinese Office Action, dated Jul. 29, 2016. In corresponding application No. 201480008866.5.
Chinese office action dated Mar. 21, 2017 from Chinese application No. 201480008866.5.
The Science Press., 200508, pp. 240-244.
Japanese Office Action dated Sep. 5, 2017, in corresponding Japanese patent application No. 2015-500308, along with English translation.

10 Claims, 13 Drawing Sheets

COMPOUND, LIGHT EMITTER, AND ORGANIC LIGHT EMITTING DEVICE

FIELD OF THE INVENTION

The present invention relates to a compound that is useful as a light emitter, and an organic light emitting device using the same.

BACKGROUND ART

An organic light emitting device, such as an organic electroluminescent device (organic EL device), has been actively studied for enhancing the light emission efficiency thereof. In particular, various studies for enhancing the light emitting efficiency have been made by newly developing and combining an electron transporting material, a hole transporting material, a light emitter and the like constituting an organic electroluminescent device. There are studies relating to an organic electroluminescent device utilizing a compound containing a heterocyclic aromatic ring, which are found among them, and some proposals have been made hitherto.

For example, Patent Document 1 describes the use of the compound represented by the following formula (I) or (II) in an organic layer present between a pair of electrodes constituting an organic electroluminescent device. In the formulae, $X^1$ and $X^2$ each represent N or CH, $Y^1$ and $Y^2$ each represent S, O or N—Z (wherein Z represents a hydrogen atom, an alkyl group, an aryl group, a cycloalkyl group or a heterocyclic group), and $R^1$ to $R^4$ each represent a halogen atom, a cyano group, a nitro group, an alkyl group, an aryl group, an alkoxy group, an aryloxy group, an alkylthio group, an arylthio group, a cycloalkyl group, an aryl group, a heterocyclic group, an amino group, an alkylamino group or an arylamino group.

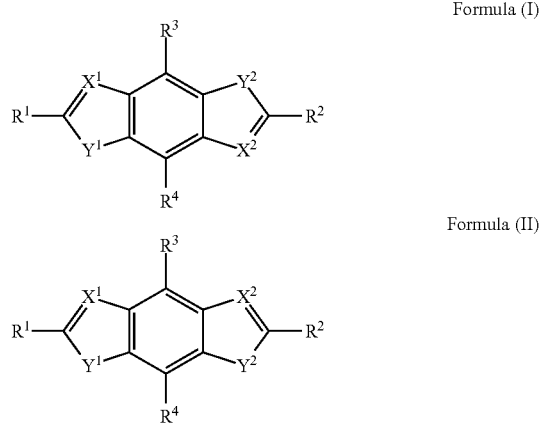

Formula (I)

Formula (II)

Patent Document 1 describes that the compound represented by the formula (I) or (II) may be used as a fluorescent emitter in a light emitting layer, and a carrier transporting material in a hole injection layer and an electron injection layer. Patent Document 1 also describes compounds having a wide variety of structures as specific examples of the compound represented by the formula (I) or (II), and among these, the compound A having the following structure is also described.

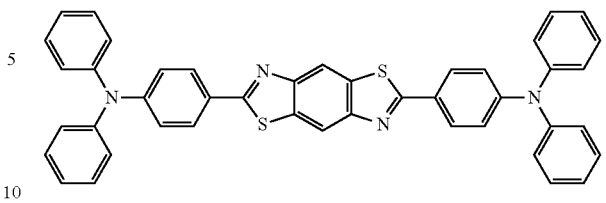

Compound A

Patent Document 2 describes the use of a compound encompassed by the formula (I) or (II) in an organic layer in an organic electroluminescent device using a phosphorescent emitter. Patent Document 2 also describes the compound A as an example compound, and is used in a hole transporting layer in the examples thereof.

CITATION LIST

Patent Documents

Patent Document 1: JP-A-10-340786
Patent Document 2: JP-A-2005-82703

SUMMARY OF INVENTION

As described above, there have been proposals of the use of the compound having the structure represented by the formula (I) or (II) in an organic electroluminescent device. However, the formulae encompass a considerably wide variety of compounds, and a wide variety of examples of the structure is described in Patent Documents 1 and 2. On the other hand, there are only a small number of compounds that have been specifically confirmed to have the effects in Patent Documents 1 and 2. In particular, as the substituent that is substituted on the aryl group in the case where $R^1$ or $R^2$ represent the aryl group in the formula (I) or (II), only a diarylamino group and the like as in the compound A are described.

However, an organic electroluminescent device that uses the compound A in a light emitting layer fails to have a high efficiency. Accordingly, there is room for improvement in the use of the same series of compounds as a light emitter. Patent Documents 1 and 2 fail to describe or suggest the relationship between the light emission efficiency as a light emitter and the structures of the same series of compounds. Consequently, it is extremely difficult to predict accurately the properties of the compounds that have analogous structures to the compounds having the effects confirmed in Patent Documents 1 and 2. Furthermore, there is room for improvement in the light emission efficiency of the compound A, the structure of which is specifically described in Patent Documents 1 and 2, but Patent Documents 1 and 2 fail to suggest the structure that is capable of improving the light emission efficiency.

The present inventors have considered the problems of the related art and have made investigations for providing a compound having a high light emission efficiency. The inventors also have made investigations for providing a formula of compounds that are useful as a light emitter and generalizing the structure of an organic light emitting device having a high light emission efficiency.

As a result of earnest investigations for achieving the objects, the inventors have succeeded in the synthesis of a group of compounds having a particular structure, and have found excellent properties of the group of compounds as a light emitter. The inventors have also found compounds that are useful as a delayed fluorescent emitter in the group of compounds, and have clarified that an organic light emitting device having a high light emission efficiency may be provided inexpensively. Based on the knowledge, the inventors have provided the following inventions as measures for solving the problems.

(1) A compound represented by the following formula (1):

D-A-D  Formula (1)

wherein:

A represents a divalent group having a structure represented by one of the following formulae (2) to (5):

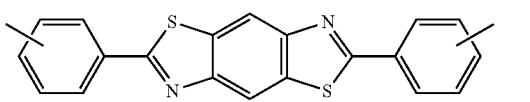
Formula (2)

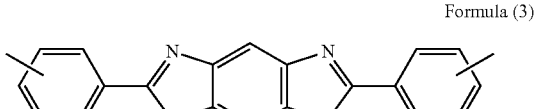
Formula (3)

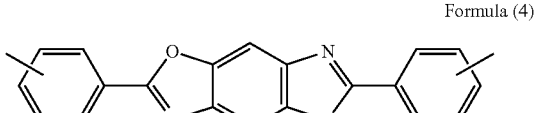
Formula (4)

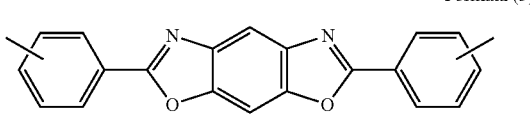
Formula (5)

in which a hydrogen atom in the structures of the formulae (2) to (5) may be substituted by a substituent; and the two groups of D each independently represent a group having a structure selected from the following structures:

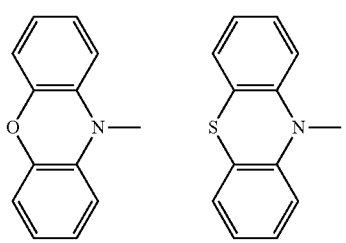

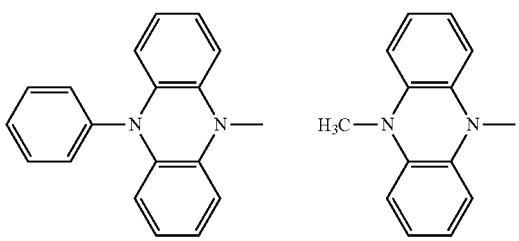

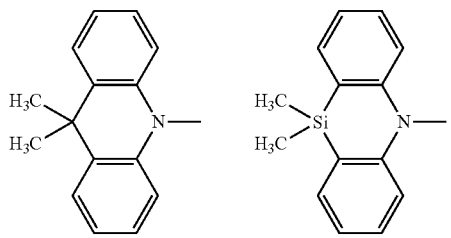

in which a hydrogen atom in the structures may be substituted by a substituent.

(2) The compound according to the item (1), wherein A in the formula (1) has a structure represented by one of the following formulae (6) to (9):

Formula (6)

Formula (7)

Formula (8)

Formula (9)

wherein $R^1$ to $R^{10}$ in the formulae (6) to (9) each independently represent a hydrogen atom or a substituent, and $R^1$ and $R^2$, $R^3$ and $R^4$, $R^5$ and $R^6$, and $R^7$ and $R^8$ each may be bonded to each other to form a cyclic structure.

(3) The compound according to the item (1) or (2), wherein the two groups of D have the same structure.

(4) The compound according to any one of the items (1) to (3), wherein D in the formula (1) has a structure represented by one of the following formulae (10) to (12):

Formula (10)

[Chemical structure: phenothiazine with substituents $R^{11}$ through $R^{18}$]

Formula (11)

[Chemical structure: phenoxazine with substituents $R^{11}$ through $R^{18}$]

Formula (12)

[Chemical structure with substituents $R^{11}$ through $R^{18}$ and $R^{21}$ through $R^{25}$]

wherein $R^{11}$ to $R^{18}$ and $R^{21}$ to $R^{25}$ in the formulae (10) to (12) each independently represent a hydrogen atom or a substituent, and $R^{11}$ and $R^{12}$, $R^{12}$ and $R^{13}$, $R^{13}$ and $R^{14}$, $R^{15}$ and $R^{16}$, $R^{16}$ and $R^{17}$, $R^{17}$ and $R^{18}$, $R^{21}$ and $R^{22}$, $R^{22}$ and $R^{23}$, $R^{23}$ and $R^{24}$, and $R^{24}$ and $R^{25}$ each may be bonded to each other to form a cyclic structure.

(5) The compound according to the item (4), wherein D has a structure represented by the formula (11).

(6) A light emitter consisting of the compound according to any one of the items (1) to (5).

(7) A delayed fluorescent emitter having a structure represented by the formula (1).

(8) An organic light emitting device containing a substrate having thereon alight emitting layer containing the light emitter according to the item (6).

(9) The organic light emitting device according to the item (8), wherein the organic light emitting device emits delayed fluorescent light.

(10) The organic light emitting device according to the item (8) or (9), wherein the organic light emitting device is an organic electroluminescent device.

The compound of the invention is useful as a light emitter. The compound of the invention includes a compound that emits delayed fluorescent light. An organic light emitting device using the compound of the invention as a light emitter is capable of achieving a high light emission efficiency.

DESCRIPTION OF EMBODIMENTS

Figure 1:
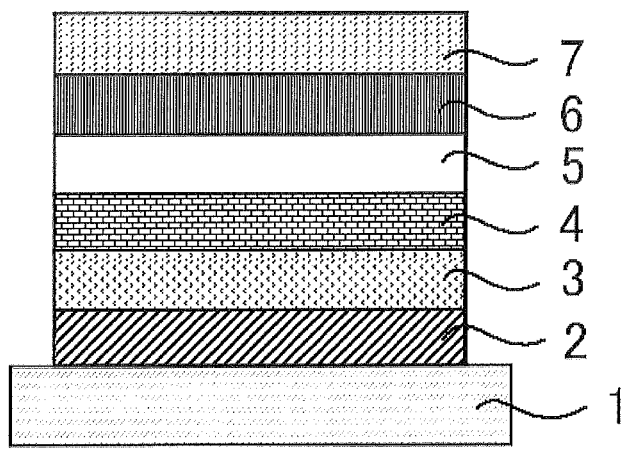
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit. In the invention, the hydrogen atom that is present in the compound used in the invention is not particularly limited in isotope species, and for example, all the hydrogen atoms in the molecule may be $^1$H, and all or a part of them may be $^2$H (deuterium (D)).

Compound represented by Formula (1)

The compound of the invention has a structure represented by the following formula (1).

D-A-D     Formula (1)

In the formula (1), A represents a divalent group having a structure represented by one of the formulae (2) to (5).

Formula (2)

[Chemical structure of benzobisthiazole with two phenyl substituents]

-continued

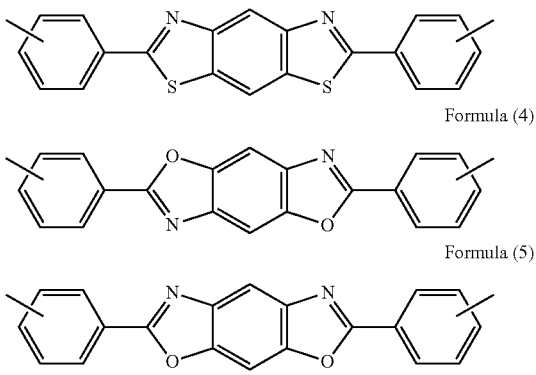

Formula (3)

Formula (4)

Formula (5)

In the aforementioned structures, a hydrogen atom may be substituted by a substituent. The number of the substituent is not particularly limited, and the substituent may not be present. In the case where two or more substituents are present, the substituents may be the same as or different from each other.

Examples of the substituent include a hydroxyl group, a halogen atom, an alkyl group having from 1 to 20 carbon atoms, an alkoxy group having from 1 to 20 carbon atoms, an alkylthio group having from 1 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, a haloalkyl group having from 1 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms and a trialkylsilylalkynyl group having from 5 to 20 carbon atoms. In these specific examples, the substituent that is capable of being further substituted with a substituent may be substituted. More preferred examples of the substituent include a substituted or unsubstituted alkyl group having from 1 to 20 carbon atoms, a substituted or unsubstituted alkoxy group having from 1 to 20 carbon atoms, a substituted or unsubstituted aryl group having from 6 to 40 carbon atoms and a substituted or unsubstituted heteroaryl group having from 3 to 40 carbon atoms. Further preferred examples of the substituent include a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms and a substituted or unsubstituted heteroaryl group having from 3 to 12 carbon atoms.

The alkyl group may be linear, branched or cyclic, and more preferably has from 1 to 6 carbon atoms, and specific examples thereof include a methyl group, an ethyl group, a propyl group, a butyl group, a tert-butyl group, a pentyl group, a hexyl group and an isopropyl group. The alkoxy group may be linear, branched or cyclic, and more preferably has from 1 to 6 carbon atoms, and specific examples thereof include a methoxy group, an ethoxy group, a propoxy group, a butoxy group, a tert-butoxy group, a pentyloxy group, a hexyloxy group and an isopropoxy group. Examples of the aryl group that is capable of being used as the substituent may be a monocyclic ring or a condensed ring, and specific examples thereof include a phenyl group and a naphthyl group. The heteroaryl group may be a monocyclic ring or a condensed ring, and specific examples thereof include a pyridyl group, a pyridazyl group, a pyrimidyl group, a triazyl group, a triazolyl group and a benzotriazolyl group. The heteroaryl group may be a group that is bonded through the hetero atom or a group that is bonded through the carbon atom constituting the heteroaryl ring.

The position bonded to D in the benzene ring at the right end in the formulae (2) to (5) may be any of the ortho-position, the meta-position and the para-position. The position bonded to D in the benzene ring at the left end in the formulae (2) to (5) may also be any of the ortho-position, the meta-position and the para-position. The positions each are preferably the meta-position or the para-position, and most preferably the para-position.

In the formula (1), A preferably represents a group having a structure represented by one of the following formulae (6) to (9):

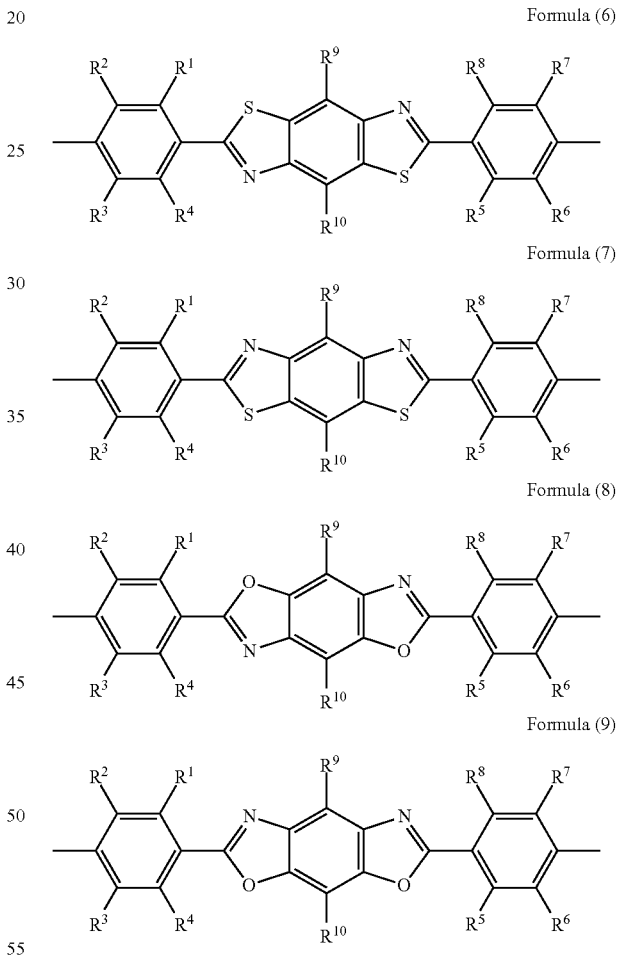

Formula (6)

Formula (7)

Formula (8)

Formula (9)

In the formulae (6) to (9), $R^1$ to $R^{10}$ each independently represent a hydrogen atom or a substituent. All $R^1$ to $R^{10}$ may be hydrogen atoms. In the case where two or more of them each are a substituent, the substituents may be the same as or different from each other. For the description and the preferred ranges of the substituent capable of being represented by $R^1$ to $R^{10}$, reference may be made to the description and the preferred ranges of the substituent capable of being represented by A in the formula (1).

$R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure. The cyclic structure may be an aromatic ring or an aliphatic ring, and may contain a hetero atom, and the cyclic structure may be a condensed ring containing two or more rings. The hetero atom referred herein is preferably selected from the group consisting of a nitrogen atom, an oxygen atom and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a triazole ring, an isothiazole ring, a cyclohexadiene ring, a cyclohexene ring, a cyclopentene ring, a cycloheptatriene ring, a cycloheptadiene ring and a cycloheptene ring.

Preferred examples of the structure represented by one of the following formulae (6) to (9) include a structure, in which all $R^1$ to $R^{10}$ are hydrogen atoms, and also include line-symmetric structures, in which $R^1$ and $R^8$, $R^2$ and $R^7$, $R^3$ and $R^6$, $R^4$ and $R^5$, and $R^9$ and $R^{10}$ each are the same as each other.

In the formula (1), the two groups of D each independently represent a group having a structure selected from the following group of structures:

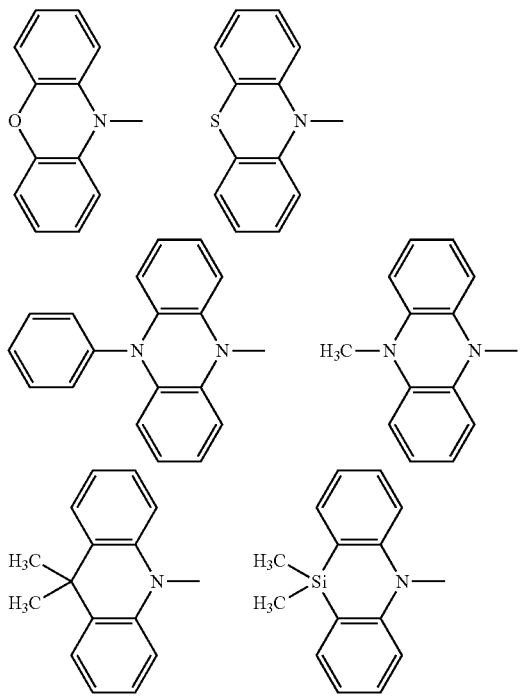

In the aforementioned group of structures, the hydrogen atom may be substituted by a substituent. In particular, the hydrogen atom that is bonded to the atom constituting the ring skeleton may be substituted by a substituent. The number of the substituent is not particularly limited, and the substituent may not be present. In the case where two or more substituents are present, the substituents may be the same as or different from each other.

Examples of the substituent, by which the hydrogen atom in the aforementioned group of structures is substituted, include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an aryl-substituted amino group having from 12 to 40 carbon atoms, an acyl group having from 2 to 20 carbon atoms, an aryl group having from 6 to 40 carbon atoms, a heteroaryl group having from 3 to 40 carbon atoms, a substituted or unsubstituted carbazolyl group having from 12 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, a substituted or unsubstituted alkoxy group having from 1 to 20 carbon atoms, a substituted or unsubstituted aryl group having from 6 to 40 carbon atoms, a substituted or unsubstituted heteroaryl group having from 3 to 40 carbon atoms, a substituted or unsubstituted dialkylamino group having from 1 to 10 carbon atoms, a substituted or unsubstituted diarylamino group having from 12 to 40 carbon atoms and a substituted or unsubstituted carbazolyl group having from 12 to 40 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted dialkylamino group having from 1 to 10 carbon atoms, a substituted or unsubstituted diarylamino group having from 12 to 40 carbon atoms, a substituted or unsubstituted aryl group having from 6 to 15 carbon atoms and a substituted or unsubstituted heteroaryl group having from 3 to 12 carbon atoms.

The hydrogen atoms that are bonded to the adjacent atoms constituting the ring skeleton in the aforementioned group of structures may be bonded to form a cyclic structure. The cyclic structure may be an aromatic ring or an aliphatic ring, and may contain a hetero atom, and the cyclic structure may be a condensed ring containing two or more rings. For the specific examples thereof, reference may be made to the specific examples of the cyclic structure in the formulae (6) to (9).

In the formula (1), D preferably represents a group having a structure represented by one of the following formulae (10) to (12):

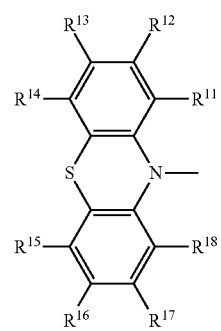

Formula (10)

-continued

Formula (11)

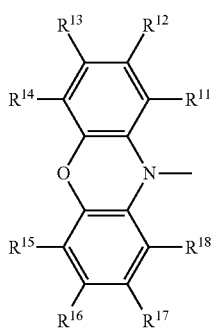

Formula (12)

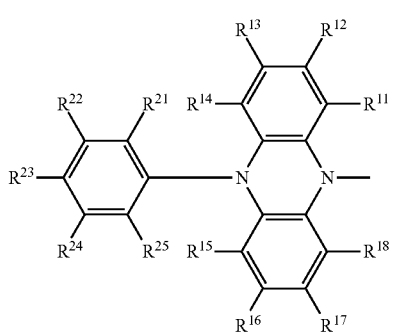

In the formulae (10) to (12), $R^{11}$ to $R^{18}$ and $R^{21}$ to $R^{25}$ each independently represent a hydrogen atom or a substituent. $R^{11}$ and $R^{12}$, $R^{12}$ and $R^{13}$, $R^{13}$ and $R^{14}$, $R^{15}$ and $R^{16}$, $R^{16}$ and $R^{17}$, $R^{17}$ and $R^{18}$, $R^{21}$ and $R^{22}$, $R^{22}$ and $R^{23}$, $R^{23}$ and $R^{24}$ and $R^{24}$ and $R^{25}$ each may be bonded to each other to form a cyclic structure.

In the formula (1), the two groups of D may be the same as or different from each other, and are preferably have the same structure. Such a case is also preferred that in the formula (1), the group of A has a symmetric structure, and two groups of D are the same as each other, so as to forma symmetric structure over the molecule.

An ordinary light emitter has a structure A-D, in which a group A functioning as an acceptor and a group D functioning as a donor are bonded to each other. On the other hand, the compound represented by the formula (1) has the structure D-A-D, in which the two groups D functioning as donors are bonded to the group A functioning as an acceptor. In the case where two or more donors D are bonded, there has ordinarily been considered a possibility that the molecule fails to function effectively as a light emitter due to balancing out the functions of the donors. In the invention, however, it has been found that the acceptor A and the donors D are carefully selected and combined, thereby providing a light emitter that has a high light emission efficiency and provides excellent effects. It is considered that this is because the spreads of HOMO and LUMO are controlled at the molecular level to satisfy the favorable conditions as a light emitter.

While the combination of A and D in the formula (1) may be arbitrarily selected, preferred examples of the compound include a compound, in which A represents a group having a structure represented by the formula (6), and D represents a group having a structure represented by (11), a compound, in which A represents a group having a structure represented by the formula (7), and D represents a group having a structure represented by (11), a compound, in which A represents a group having a structure represented by the formula (8), and D represents a group having a structure represented by (11), a compound, in which A represents a group having a structure represented by the formula (9), and D represents a group having a structure represented by (11), a compound, in which A represents a group having a structure represented by the formula (6), and D represents a group having a structure represented by (10), and a compound, in which A represents a group having a structure represented by the formula (6), and D represents a group having a structure represented by (12).

Specific examples of the compound represented by the formula (1) shown below. However, the compound represented by the formula (1) capable of being used in the invention is not construed as being limited to the specific examples.

Compound 1

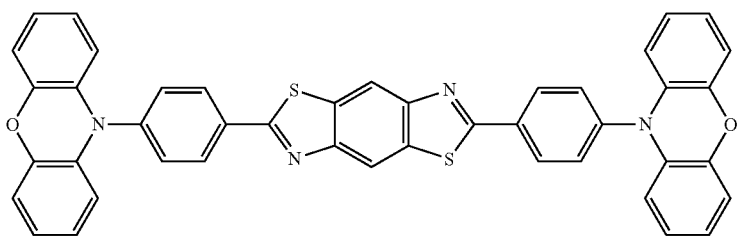

Compound 2

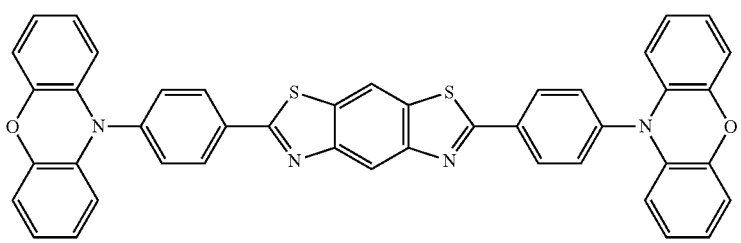

-continued
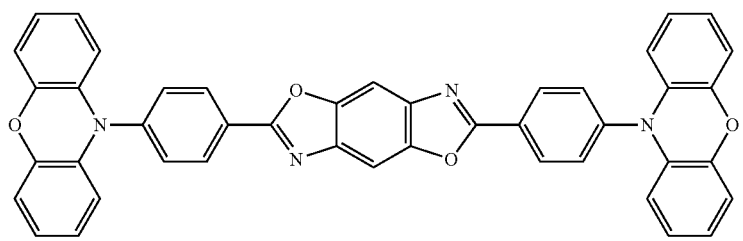
Compound 3
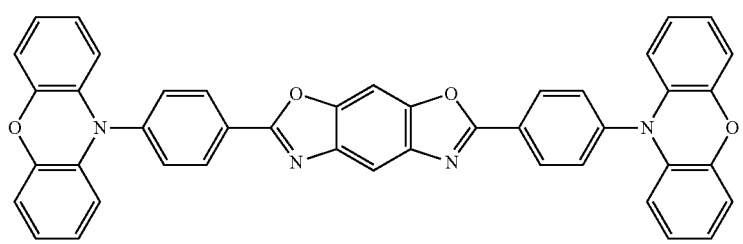
Compound 4
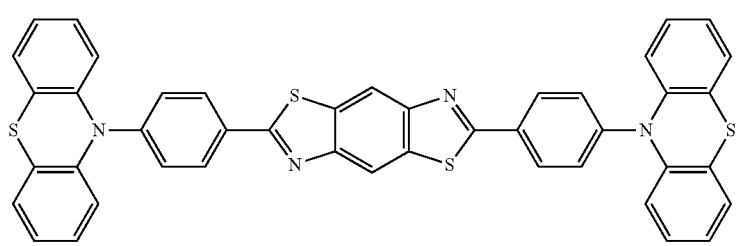
Compound 5
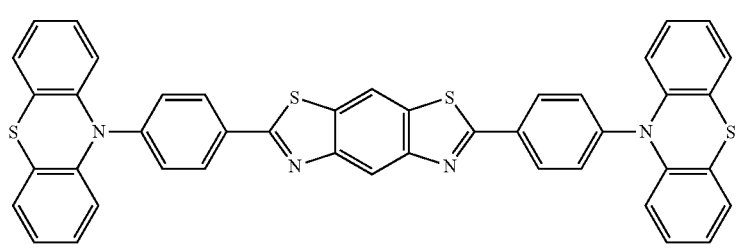
Compound 6
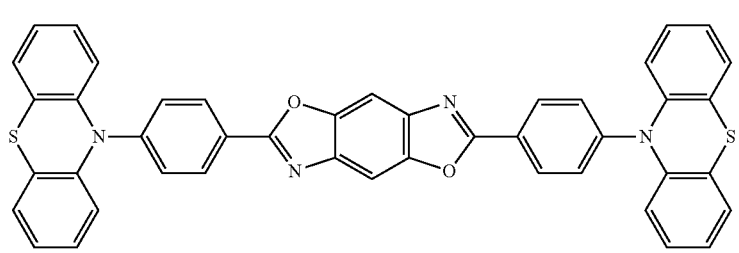
Compound 7
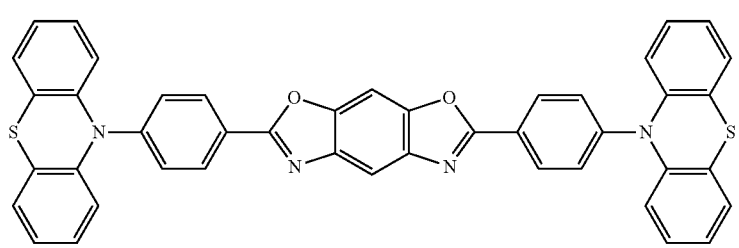
Compound 8

-continued
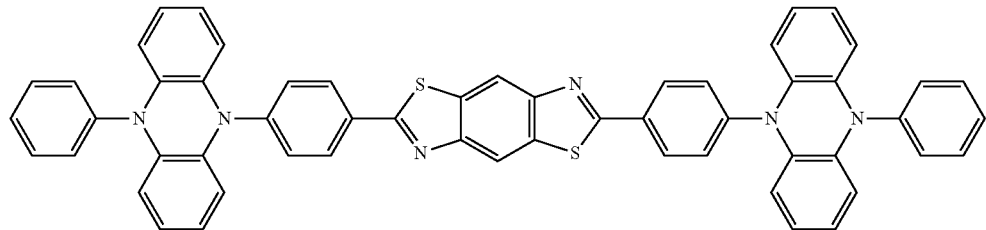
Compound 9
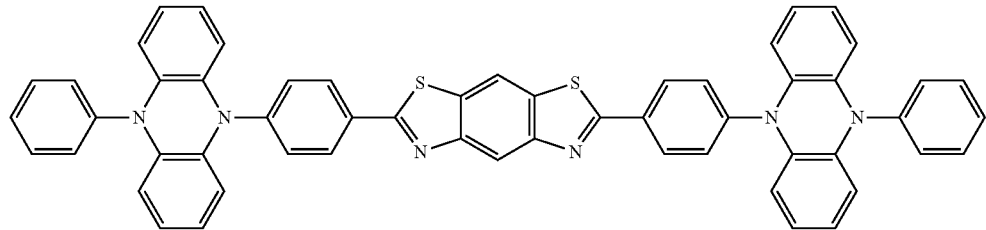
Compound 10
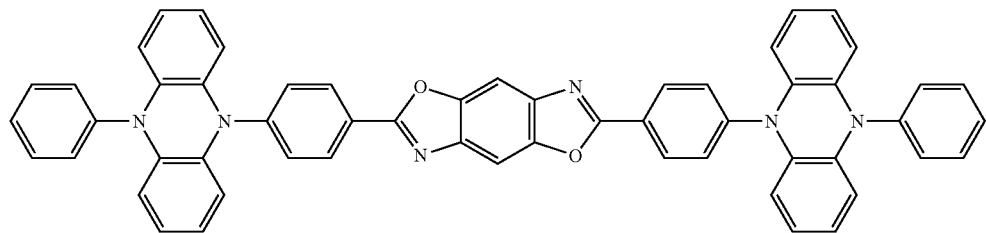
Compound 11
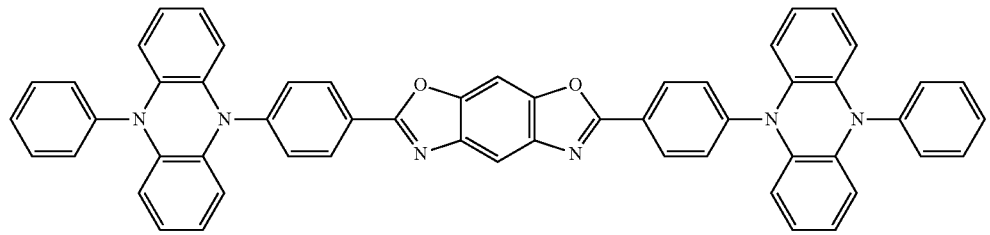
Compound 12
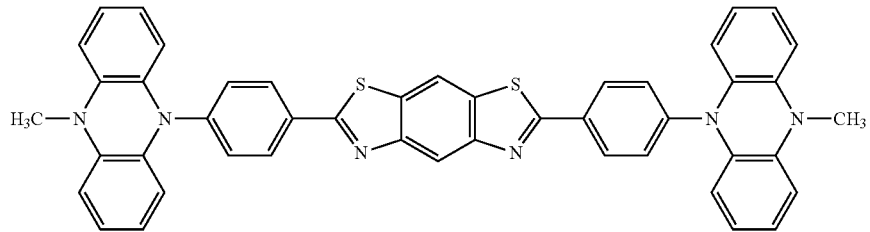
Compound 13
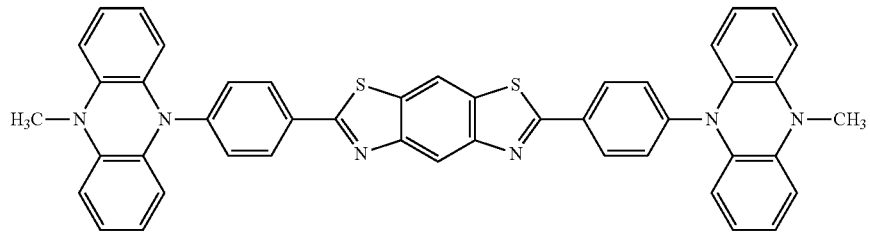
Compound 14

-continued
Compound 15
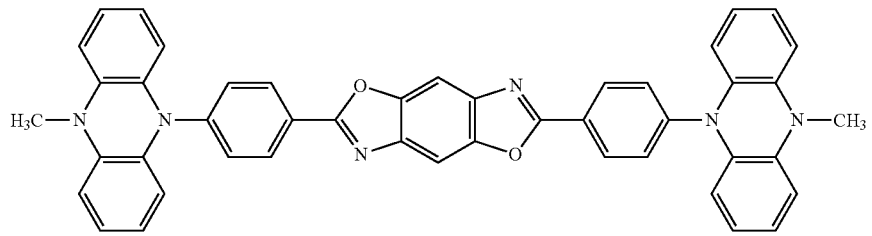
Compound 16
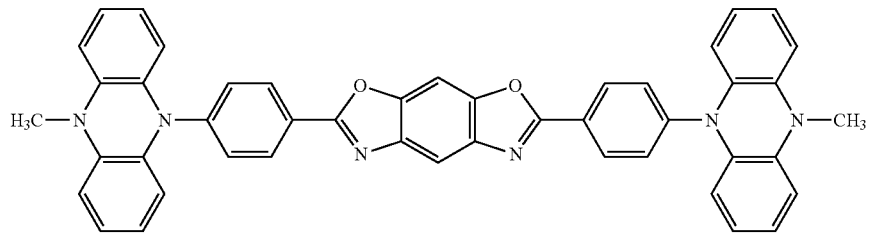
Compound 17
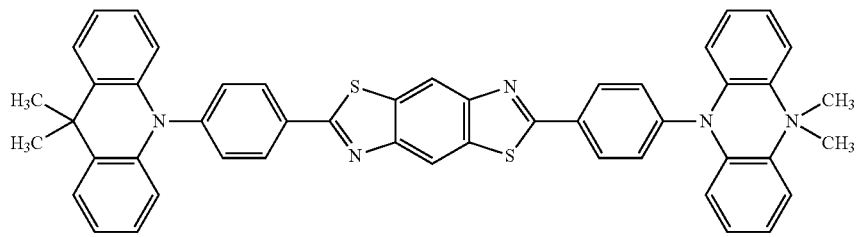
Compound 18
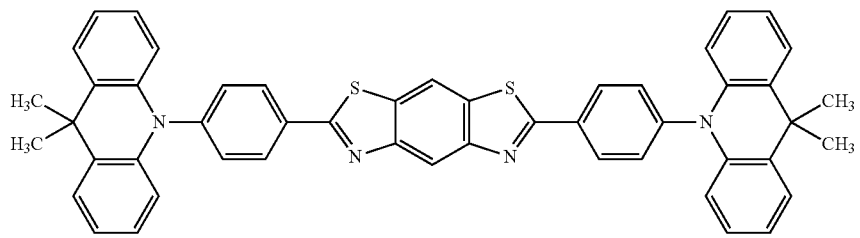
Compound 19
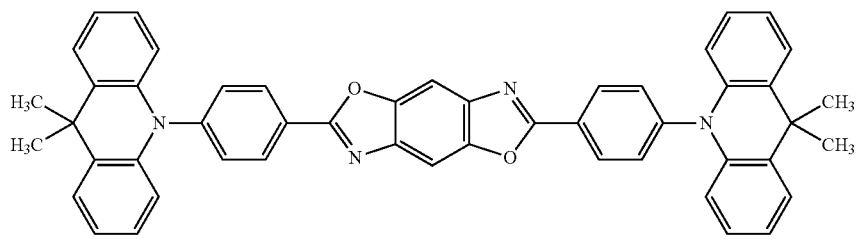
Compound 20
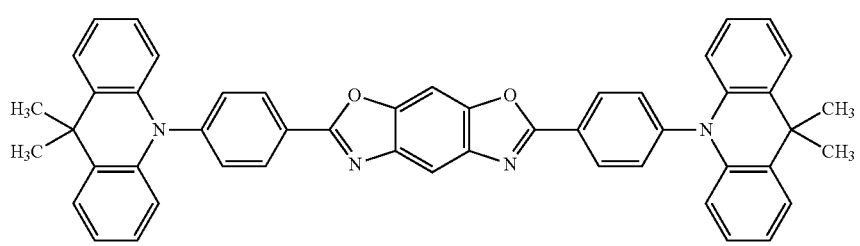

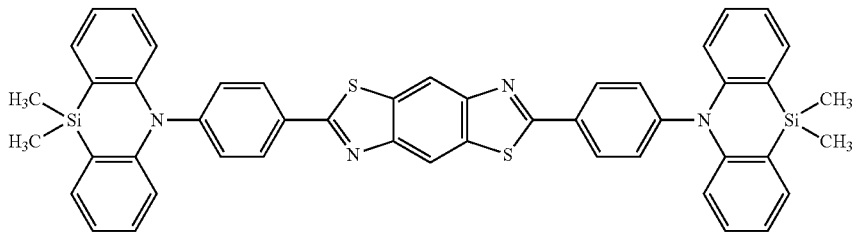

Compound 21

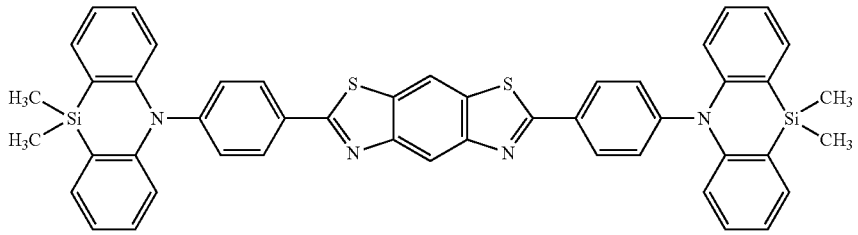

Compound 22

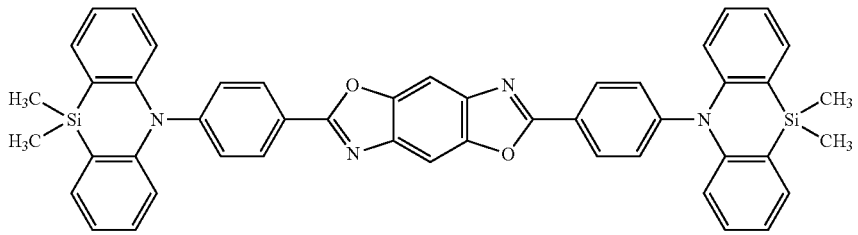

Compound 23

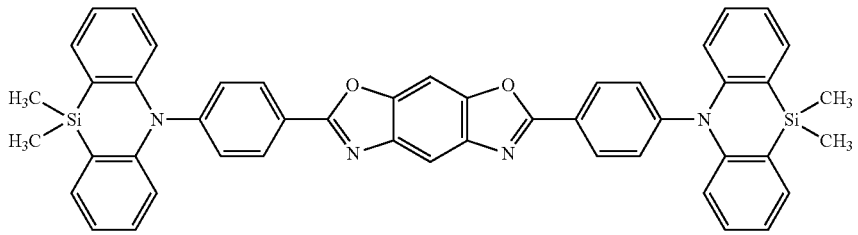

Compound 24

The molecular weight of the compound represented by the formula (1) is preferably 1,500 or less, more preferably 1,200 or less, further preferably 1,000 or less, and still further preferably 800 or less, for example, in the case where an organic layer containing the compound represented by the formula (1) is intended to be formed as a film by a vapor deposition method. The lower limit of the molecular weight is the molecular weight of the smallest compound represented by the formula (1).

The compound represented by the formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the formula (1) in the molecule is used as a light emitter.

For example, it may be considered that a polymerizable group is introduced in advance to the structure represented by the formula (1), and a polymer obtained by polymerizing the polymerizable group is used as a light emitter. Specifically, it may be considered that a monomer that has a polymerizable functional group at any of A and D in the formula (1) is prepared, and is homopolymerized or copolymerized with another monomer to prepare a polymer containing repeating units, and the polymer is used as a light emitter. In alternative, it may be considered that the compounds represented by the formula (1) are reacted to form a dimer or a trimer, and the dimer or the trimer is used as a light emitter.

Examples of the polymer having the repeating unit containing the structure represented by the formula (1) include a polymer containing a structure represented by the following formula (13) or (14).

Formula (13)

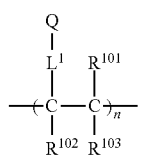

Formula (14)

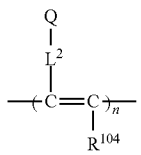

In the formulae (13) and (14), Q represents a group containing the structure represented by the formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by —$X^{11}$-$L^{11}$-, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the formulae (13) and (14), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of A and D in the structure represented by the formula (1) constituting Q, $R^1$ to $R^{10}$ in the structures represented by the formulae (6) to (9), and $R^{11}$ to $R^{18}$ and $R^{21}$ to $R^{28}$ in the structures represented by the formulae (10) to (12). Two or more of the linking groups may be boded to one group represented by Q to form a crosslinked structure or a network structure.

Specific examples of the structure of the repeating unit include structures represented by the following formulae (15) to (18).

Formula (15)

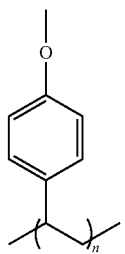

Formula (16)

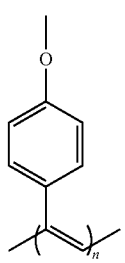

Formula (17)

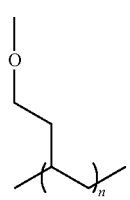

Formula (18)

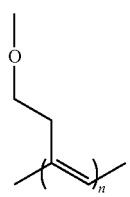

The polymer having the repeating unit containing the structure represented by any of the formulae (15) to (18) may be synthesized in such a manner that a hydroxyl group is introduced to any of A and D in the structure represented by the formula (1), and the hydroxyl group as a linker is reacted with the following compound to introduce a polymerizable group thereto, followed by polymerizing the polymerizable group.

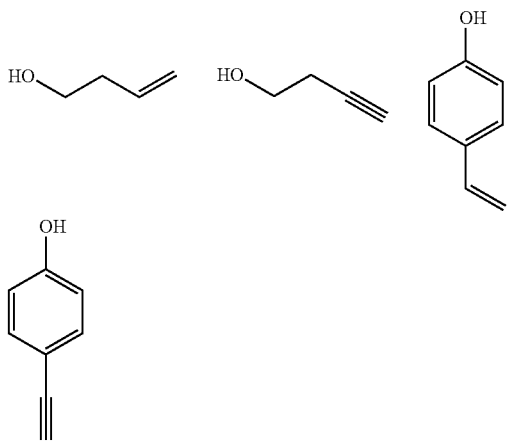

The polymer containing the structure represented by the formula (1) in the molecule may be a polymer containing only a repeating unit having the structure represented by the formula (1), or a polymer further containing a repeating unit having another structure. The repeating unit having the structure represented by the formula (1) contained in the polymer may be only one kind or two or more kinds. Examples of the repeating unit that does not have the structure represented by the formula (1) include a repeating unit derived from a monomer that is used for ordinary copolymerization. Examples of the repeating unit include a repeating unit derived from a monomer having an ethylenic unsaturated bond, such as ethylene and styrene.

Synthesis Method of Compound Represented by Formula (1)

The compound represented by the formula (1) may be synthesized by combining the known reactions. For example, the compound may be synthesized through the following scheme.

In the aforementioned reaction scheme, for the descriptions of A and D, reference may be made to the corresponding descriptions in the formula (1). In the reaction scheme, X represents a halogen atom, examples of which include a fluorine atom, a chlorine atom, a bromine atom and an iodine atom, with a chlorine atom, a bromine atom and an iodine atom being preferred.

In the compound represented by the formula (1), for example, a compound, in which A represents a group having a structure represented by the formula (6), and D represents a group having a structure represented by (11), may be synthesized through the following scheme.

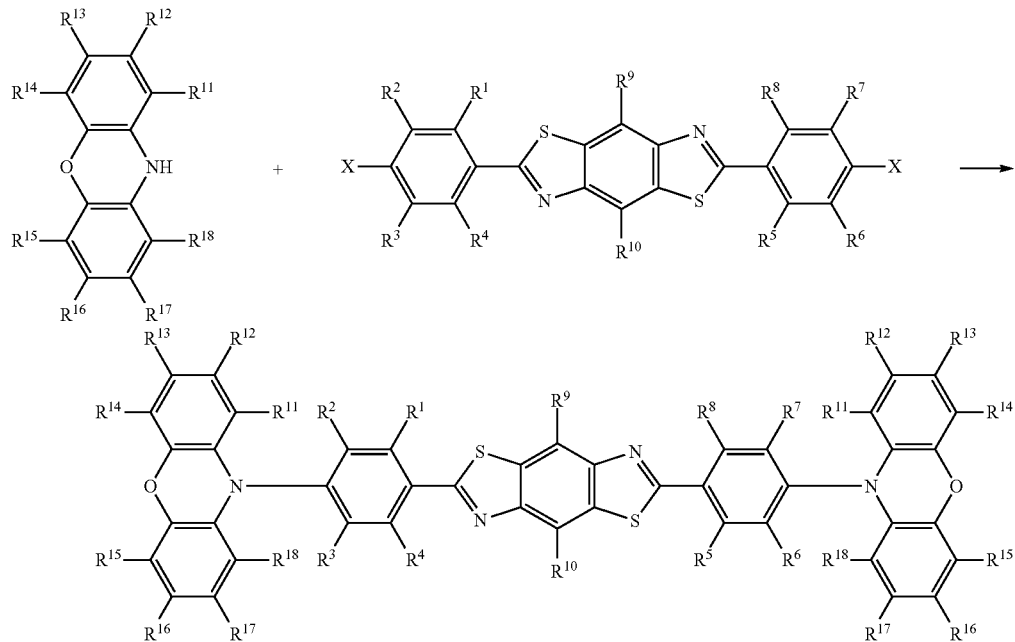

In the aforementioned reaction scheme, for the descriptions of $R^1$ to $R^{18}$, reference may be made to the corresponding descriptions in the formulae (6) and (11). In the reaction scheme, X represents a halogen atom.

The reactions shown by the two reaction schemes are applications of the known reaction, and the known reaction conditions may be appropriately selected and used. For the details of the reactions, reference may be made to the synthesis examples described later. The compound represented by the formula (1) may also be synthesized by combining the other known synthesis reactions.

Organic Light Emitting Device

The compound represented by the formula (1) of the invention is useful as a light emitter of an organic light emitting device. Accordingly, the compound represented by the formula (1) of the invention may be effectively used as a light emitter in a light emitting layer of an organic light emitting device. The compound represented by the formula (1) includes a delayed fluorescent emitter emitting delayed fluorescent light. Thus, the invention provides an invention relating to a delayed fluorescent emitter having the structure represented by the formula (1), an invention relating to the use of the compound represented by the formula (1) as the delayed fluorescent emitter, and an invention relating to a method for emitting delayed fluorescent light with the compound represented by the formula (1). An organic light emitting device that uses the compound as a light emitter has features that the device emits delayed fluorescent light and has a high light emission efficiency. The principle of the features may be described as follows for an organic electroluminescent device as an example.

In an organic electroluminescent device, carriers are injected from an anode and a cathode to a light emitter to form an excited state for the light emitter, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy use efficiency. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent emitter emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent emitter emitting light through absorption of thermal energy is particularly useful for an organic electroluminescent device. In the case where a delayed fluorescent emitter is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the formula (1) of the invention as a light emitter of a light emitting layer may provide an excellent organic light emitting device, such as an organic photoluminescent device (organic PL device) and an organic electroluminescent device (organic EL device). At this time, the compound represented by the formula (1) of the invention may have a function of assisting light emission of another light emitter contained in the light emitting layer, i.e., as a so-called assist dopant. Specifically, the compound represented by the formula (1) of the invention contained in the light emitting layer may have a lowest excited singlet energy level that is between the lowest excited singlet energy level of the host material contained in the light emitting layer and the lowest excited singlet energy level of the another light emitter contained in the light emitting layer.

The organic photoluminescent device has a structure containing a substrate having formed thereon at least a light emitting layer. The organic electroluminescent device has a structure containing at least an anode, a cathode and an organic layer formed between the anode and the cathode. The organic layer contains at least a light emitting layer, and may be formed only of a light emitting layer, or may have one or more organic layer in addition to the light emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light emitting layer, 6 denotes an electron transporting layer, and 7 denotes a cathode.

The members and the layers of the organic electroluminescent device will be described below. The descriptions for the substrate and the light emitting layer may also be applied to the substrate and the light emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness thereof may be generally selected from a range of from 10 to 1,000 nm, and preferably from 10 to 200 nm, while depending on the material used.

Cathode

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light Emitting Layer

The light emitting layer is a layer, in which holes and electrons injected from the anode and the cathode, respectively, are recombined to form excitons, and then the layer emits light. A light emitter may be solely used as the light emitting layer, but the light emitting layer preferably contains a light emitter and a host material. The light emitter used may be one kind or two or more kinds selected from the group of compounds represented by the formula (1) of the invention. In order that the organic electroluminescent device and the organic photoluminescent device of the invention exhibit a high light emission efficiency, it is important that the singlet excitons and the triplet excitons generated in the light emitter are confined in the light emitter. Accordingly, a host material is preferably used in addition to the light emitter in the light emitting layer. The host material used may be an organic compound that has excited singlet energy and excited triplet energy, at least one of which is higher than those of the light emitter of the invention. As a result, the singlet excitons and the triplet excitons generated in the light emitter of the invention are capable of being confined in the molecules of the light emitter of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light emitting device and the organic electroluminescent device of the invention, the light emission occurs in the light emitter of the invention contained in the light emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light emitter contained in the light emitting layer is preferably 0.1% by weight or more, and more preferably 1% by weight or more, and is preferably 50% by weight or less, more preferably 20% by weight or less, and further preferably 10% by weight or less.

The host material in the light emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light emitting layer or the hole transporting layer and between the cathode and the light emitting layer or the electron transporting layer. The injection layer may be provided depending on necessity.

Barrier Layer

The barrier layer is a layer that is capable of inhibiting charges (electrons or holes) and/or excitons present in the light emitting layer from being diffused outside the light emitting layer. The electron barrier layer may be disposed between the light emitting layer and the hole transporting layer, and inhibits electrons from passing through the light emitting layer toward the hole transporting layer. Similarly, the hole barrier layer may be disposed between the light emitting layer and the electron transporting layer, and inhibits holes from passing through the light emitting layer toward the electron transporting layer. The barrier layer may also be used for inhibiting excitons from being diffused outside the light emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light emitting layer.

Exciton Barrier Layer

The exciton barrier layer is a layer for inhibiting excitons generated through recombination of holes and electrons in the light emitting layer from being diffused to the charge transporting layer, and the use of the layer inserted enables effective confinement of excitons in the light emitting layer, and thereby enhances the light emission efficiency of the device. The exciton barrier layer may be inserted adjacent to the light emitting layer on any of the side of the anode and the side of the cathode, and on both the sides. Specifically, in the case where the exciton barrier layer is present on the side of the anode, the layer may be inserted between the hole transporting layer and the light emitting layer and adjacent to the light emitting layer, and in the case where the layer is inserted on the side of the cathode, the layer may be inserted between the light emitting layer and the cathode and adjacent to the light emitting layer. Between the anode and the exciton barrier layer that is adjacent to the light emitting layer on the side of the anode, a hole injection layer, an electron barrier layer and the like may be provided, and between the cathode and the exciton barrier layer that is adjacent to the light emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the formula (1) may be used not only in the light emitting layer but also in the other layers than the light emitting layer. In this case, the compound represented by the formula (1) used in the light emitting layer and the compound represented by the formula (1) used in the other layers than the light emitting layer may be the same as or different from each other. For example, the compound represented by the formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R and $R_1$ to $R_7$ each independently represent a hydrogen atom or a substituent, and n represents an integer of from 3 to 5.

Preferred examples of a compound that may also be used as the host material of the light emitting layer are shown below.

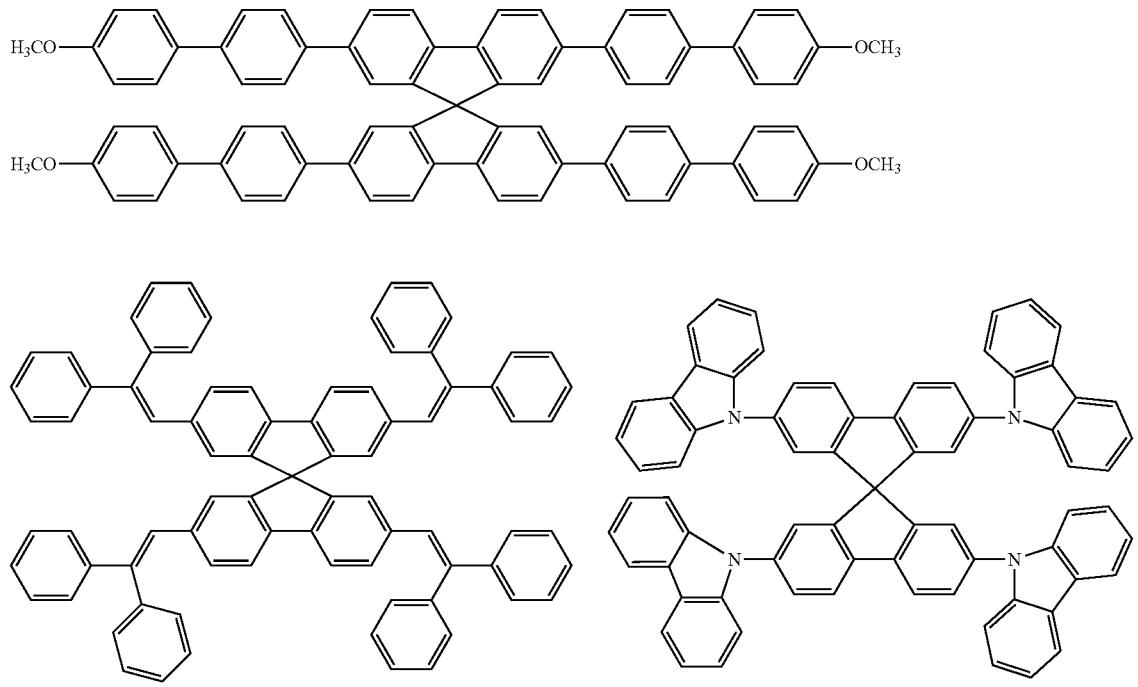

-continued
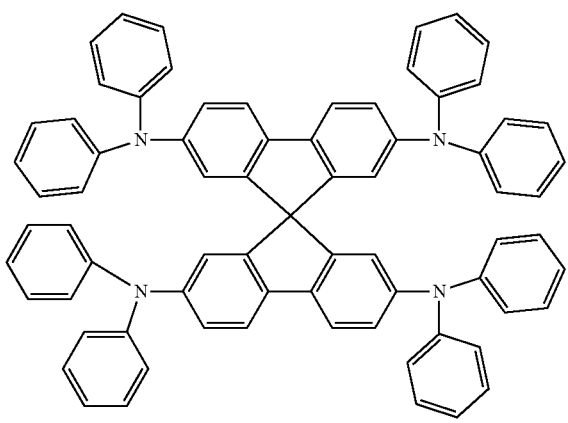
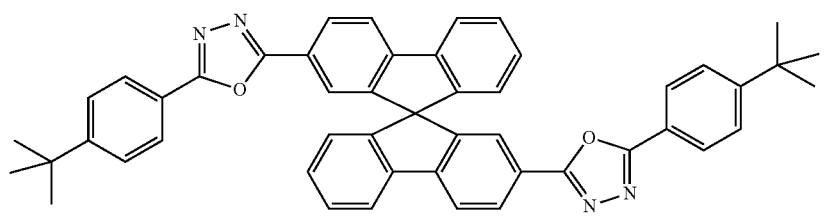
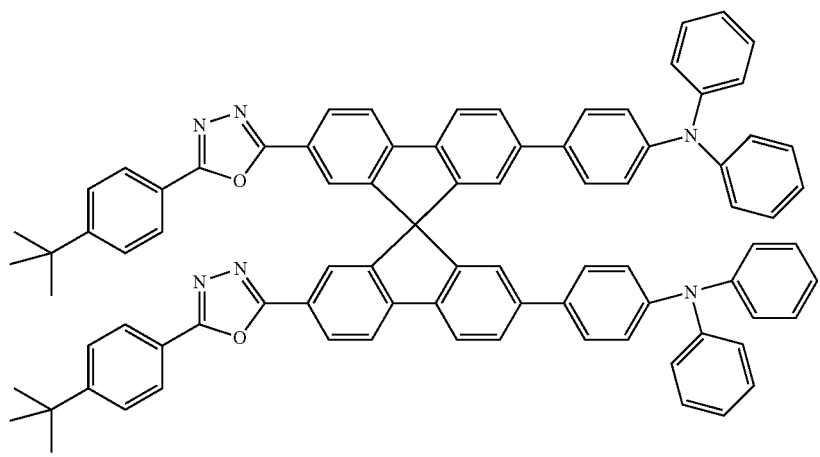
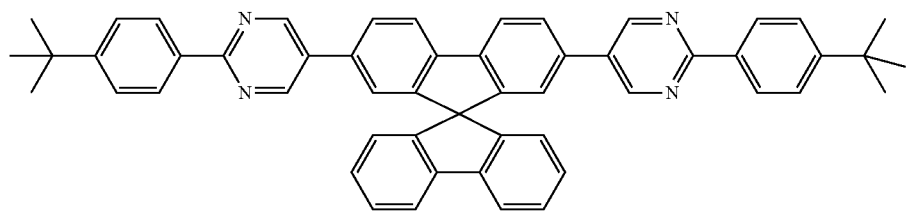
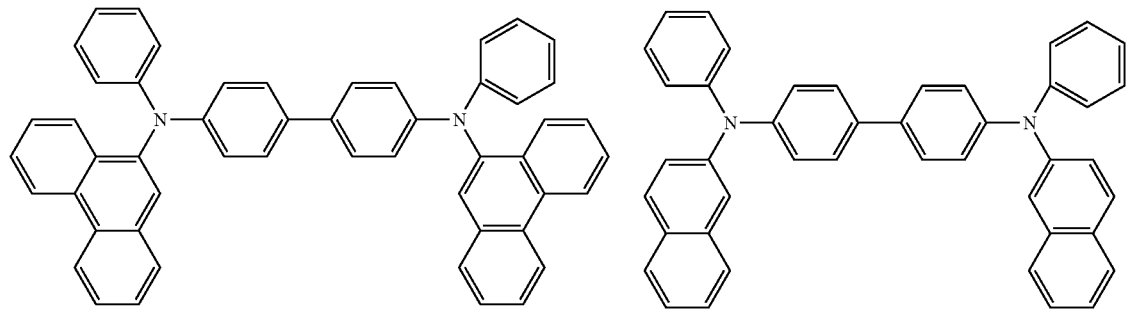

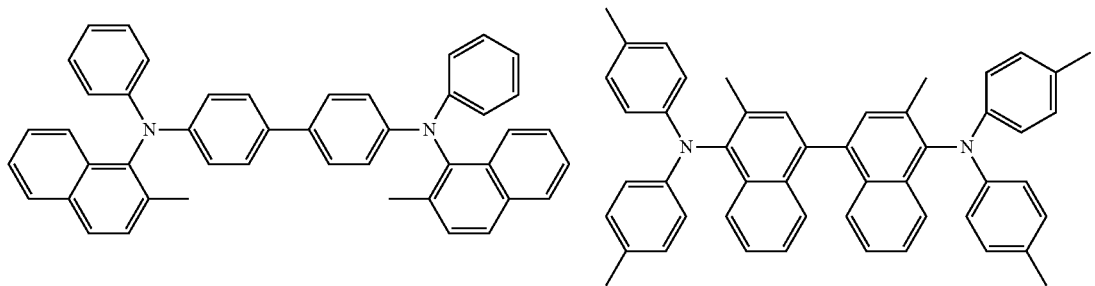
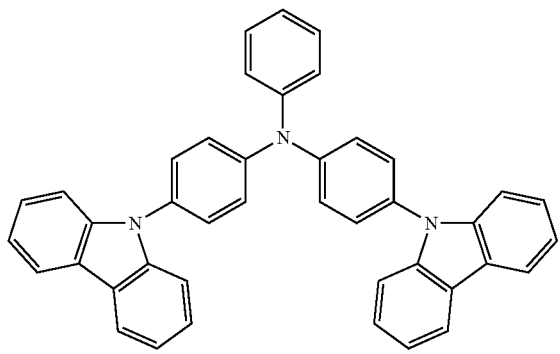
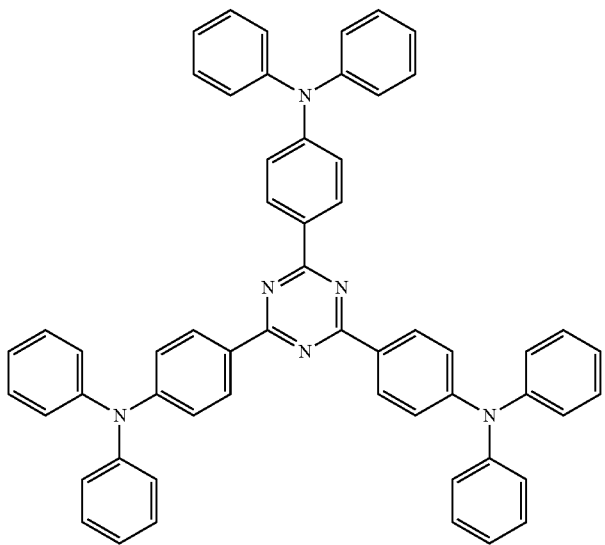

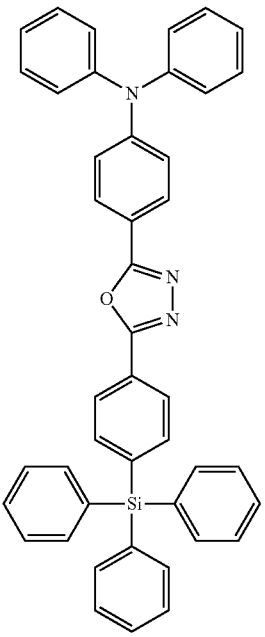
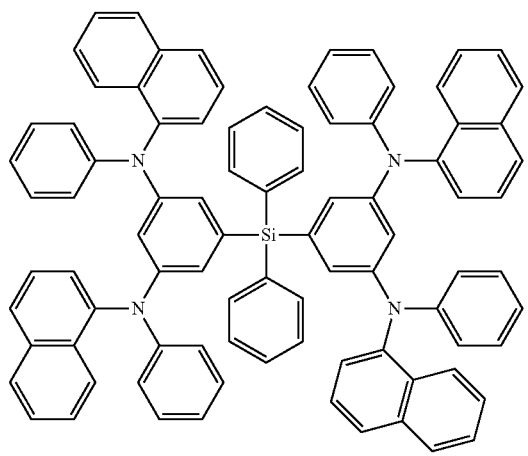
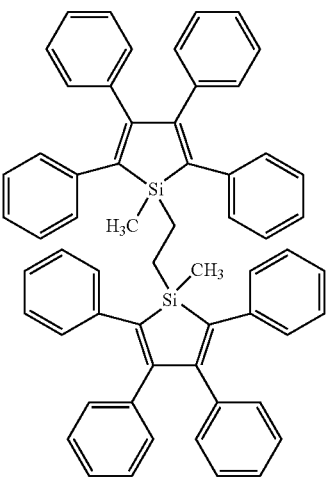
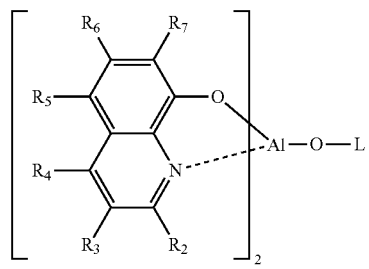
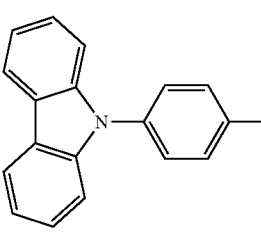
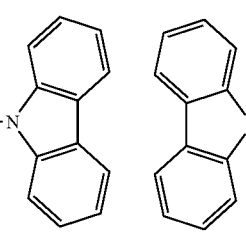

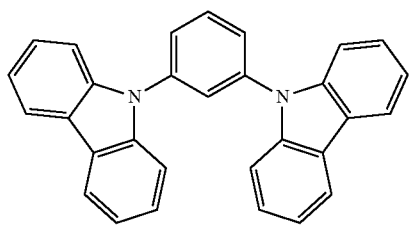
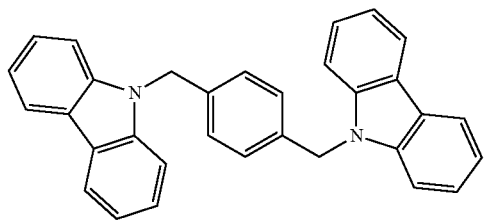
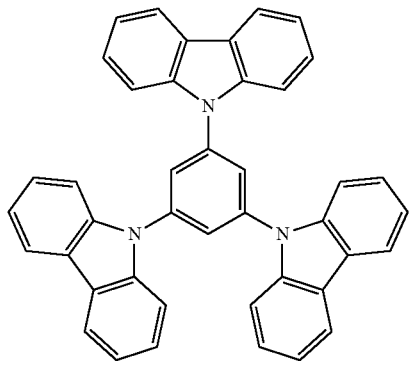
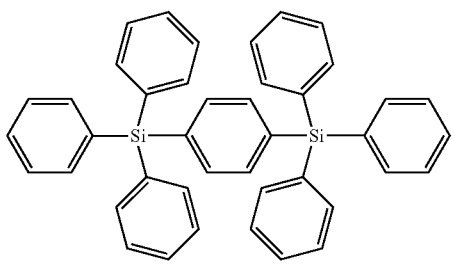
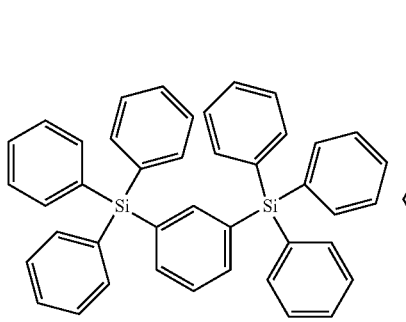
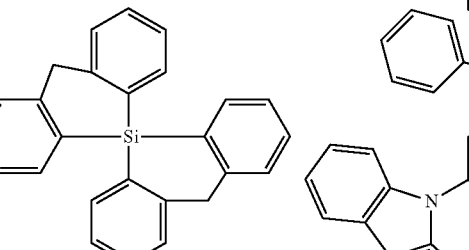
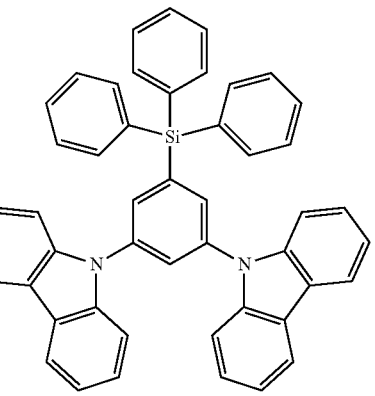
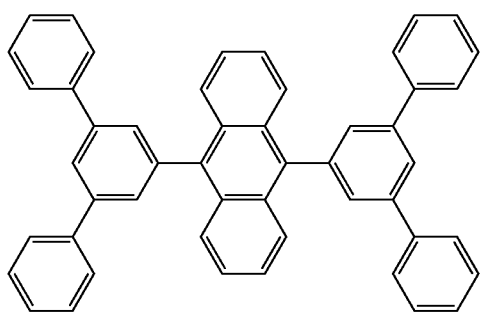
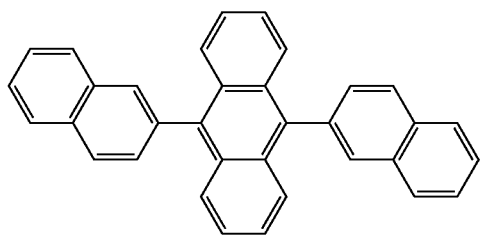
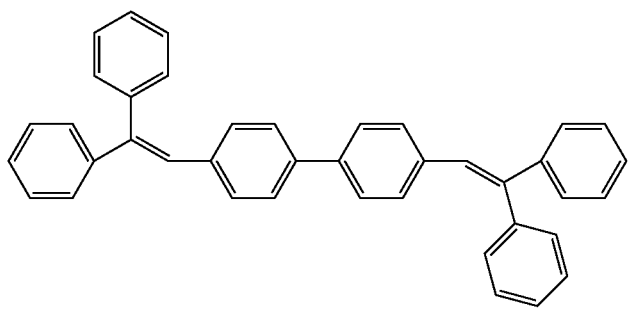

-continued
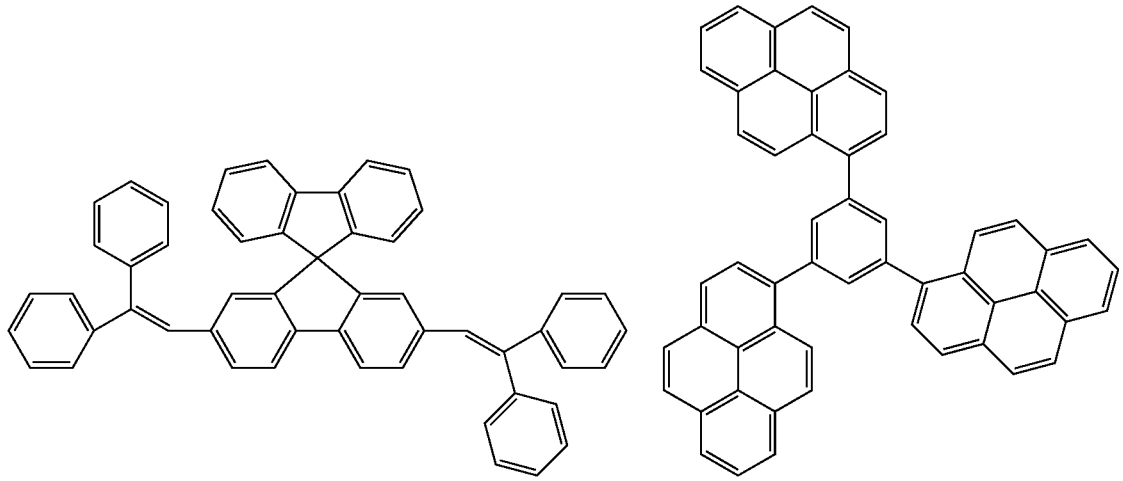
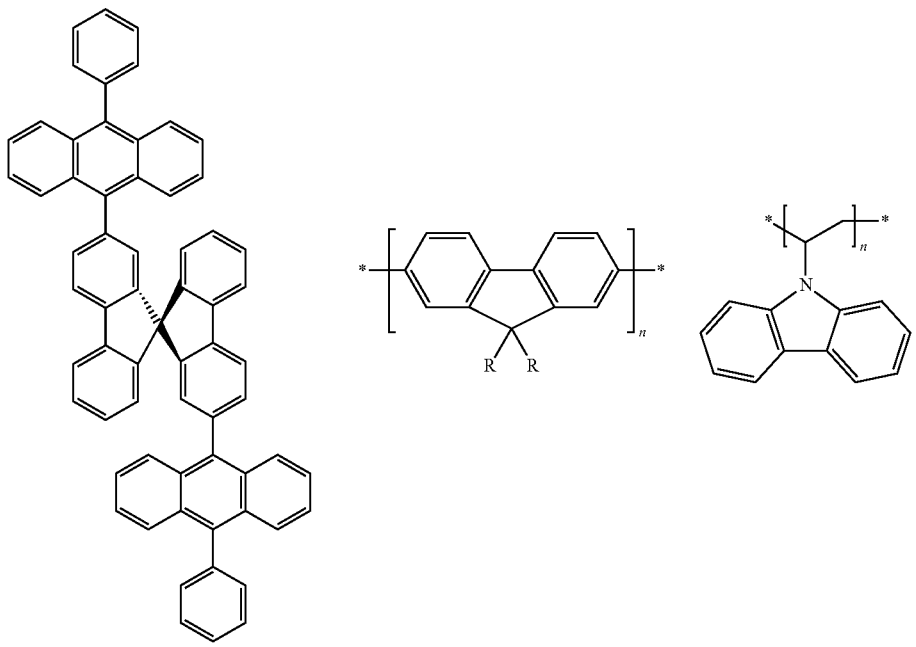
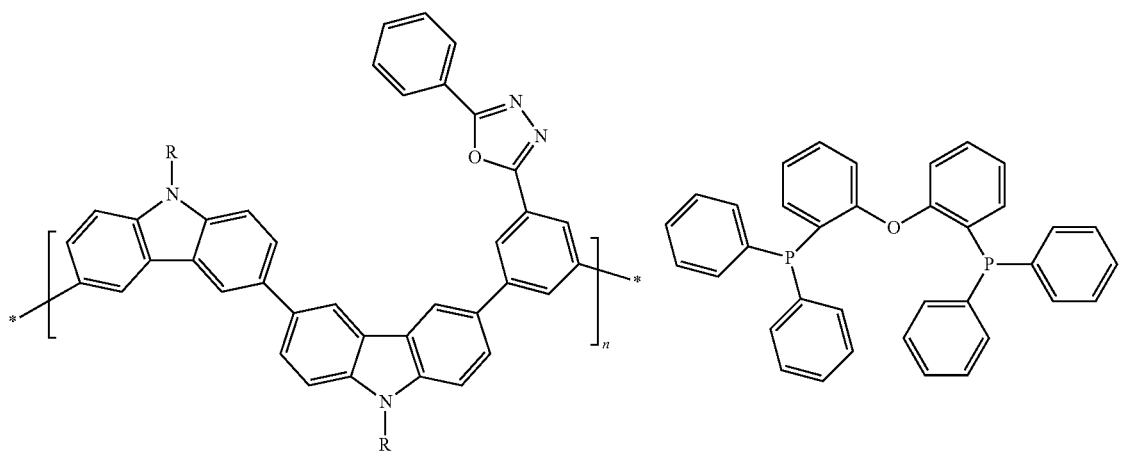

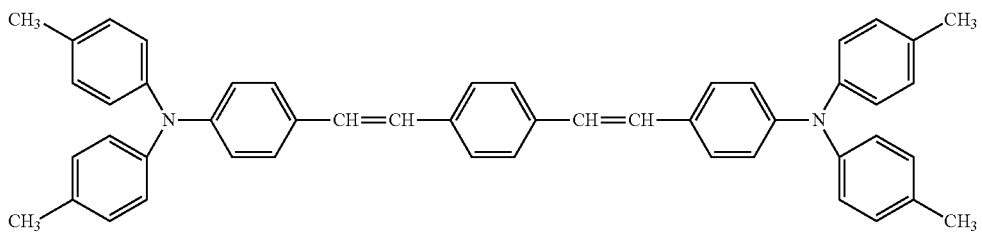
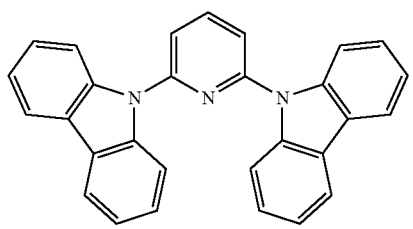
Preferred examples of a compound that may be used as the hole injection material are shown below.
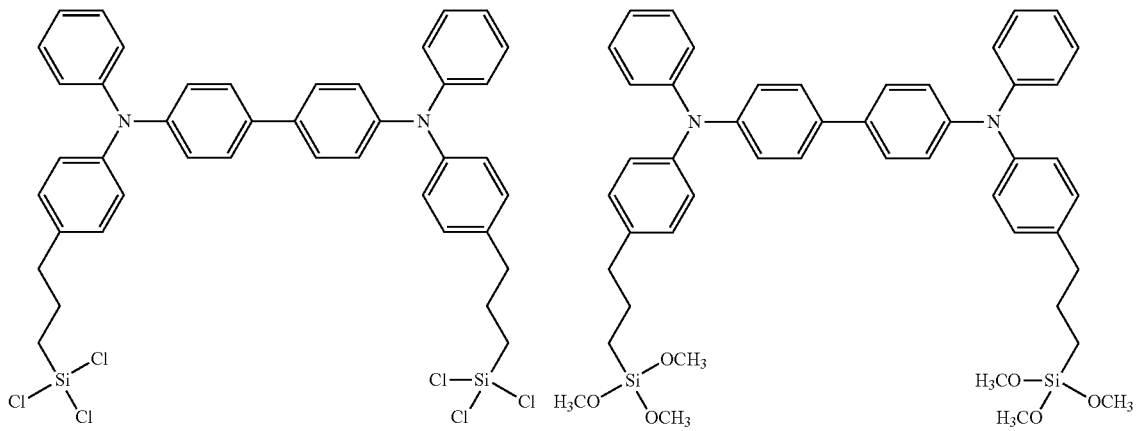
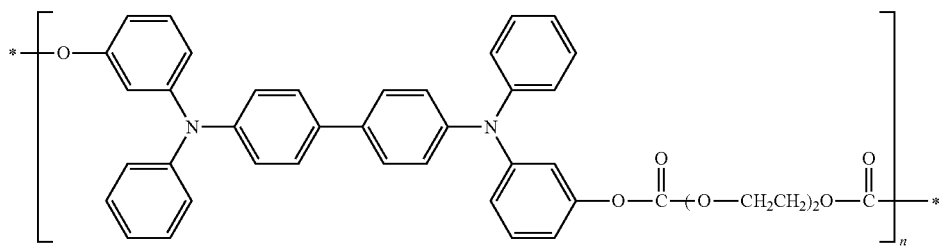

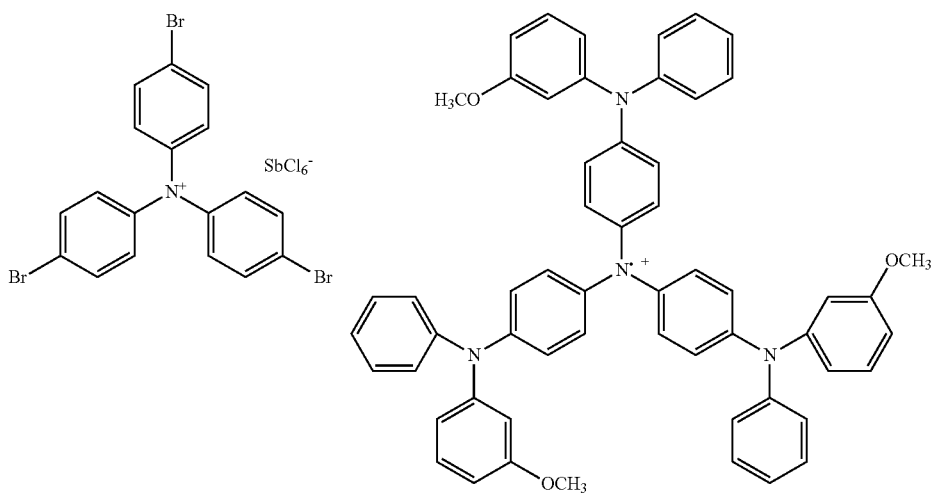
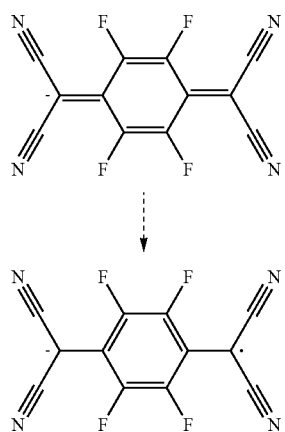
Preferred examples of a compound that may be used as the hole transporting material are shown below.
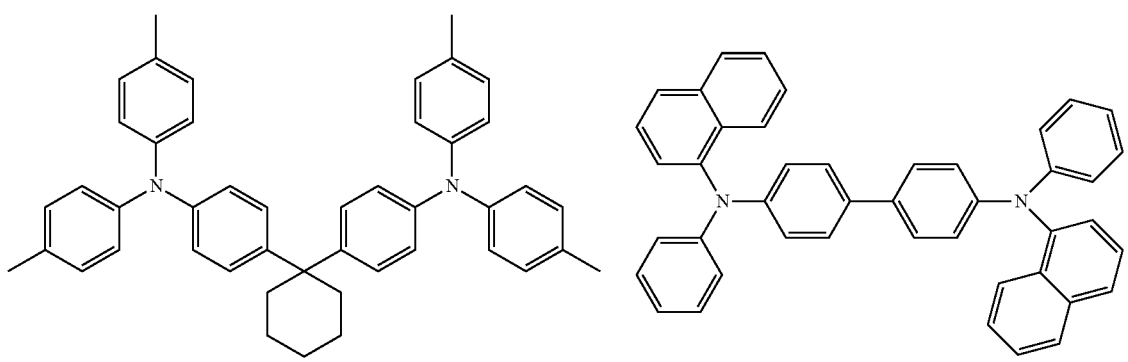

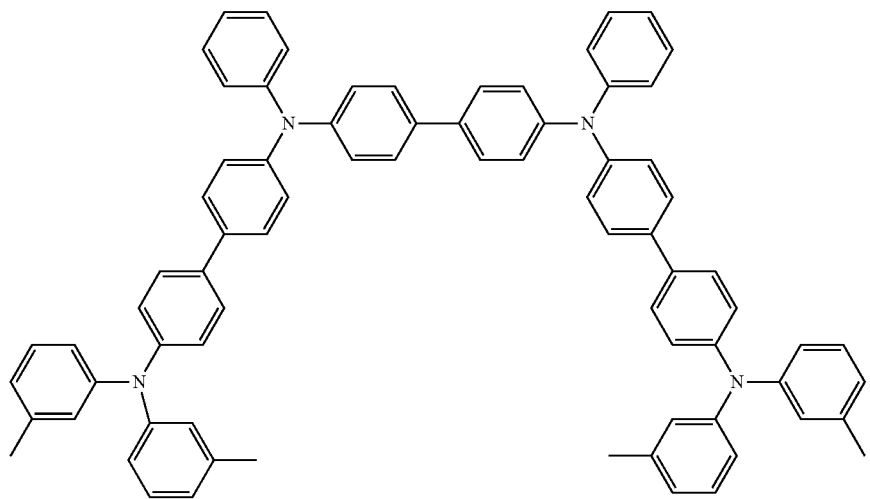
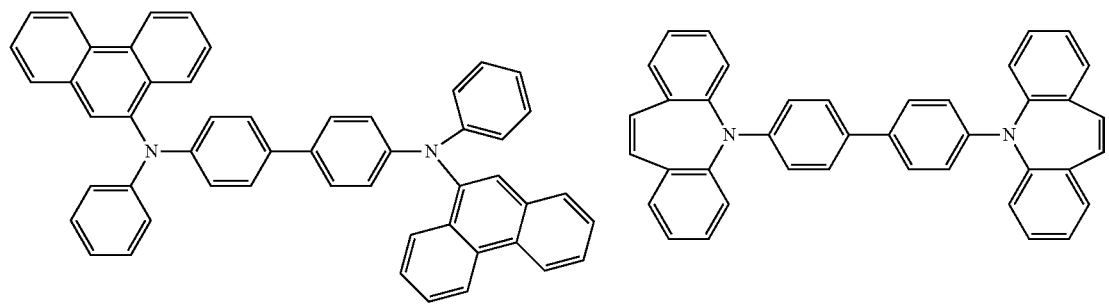
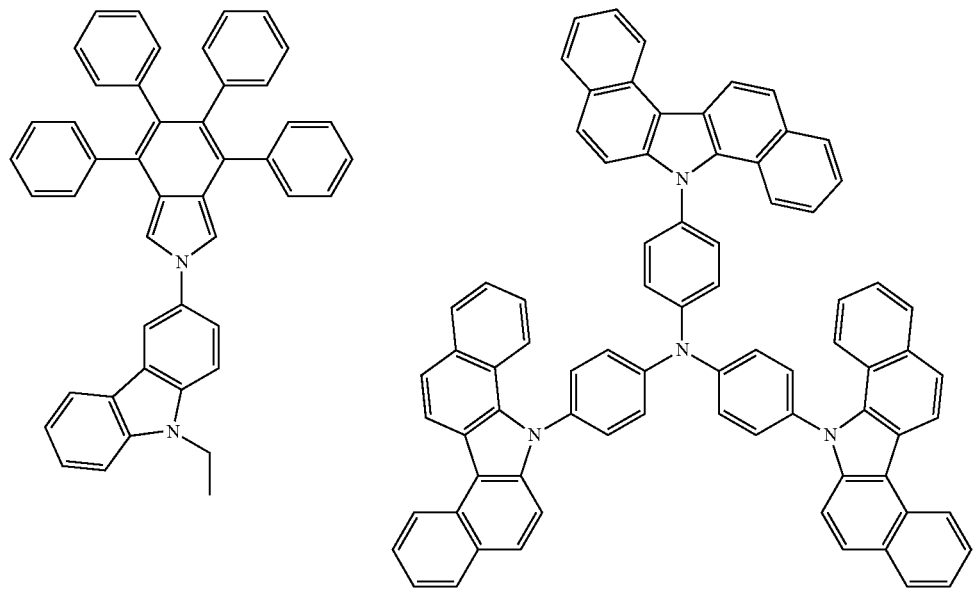

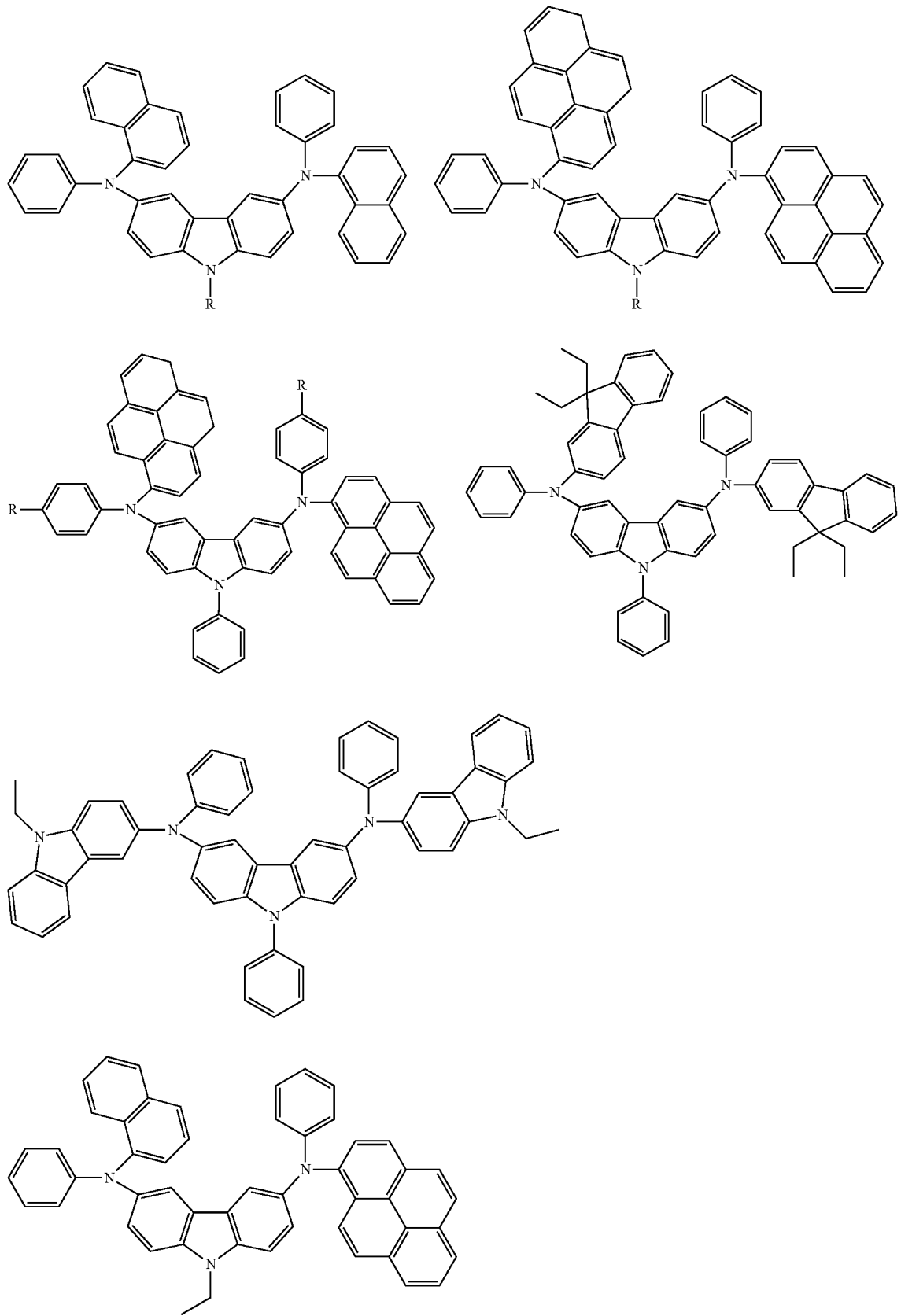

-continued
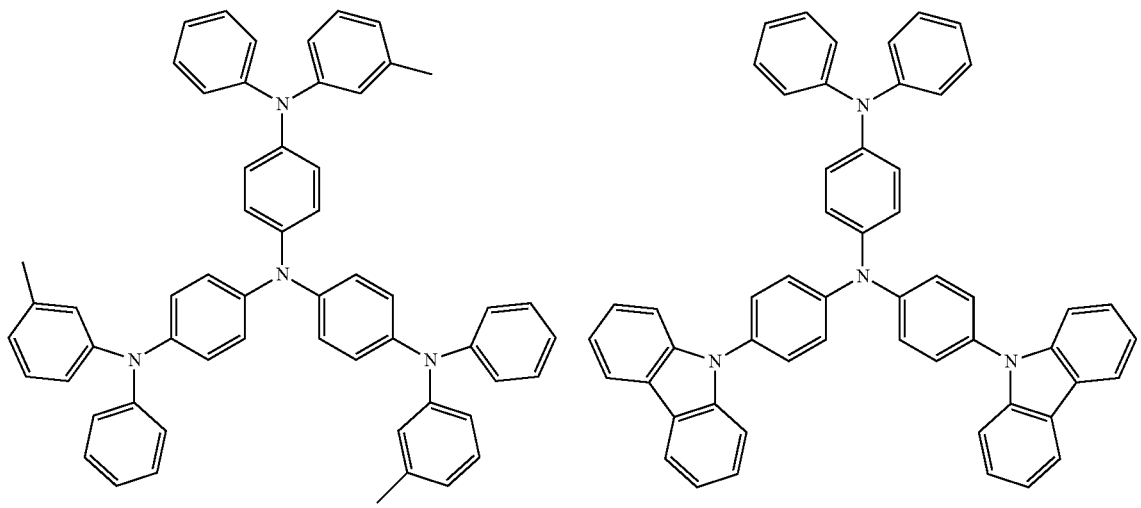
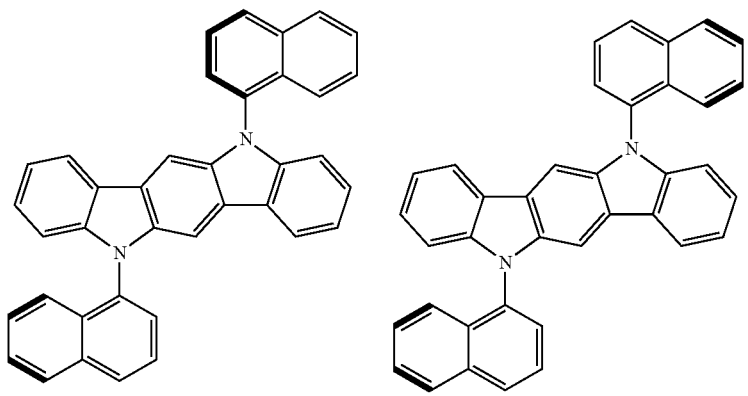
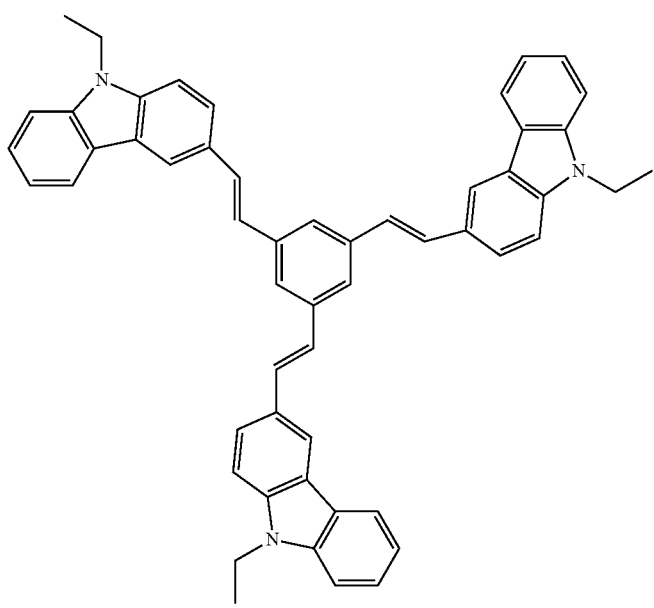

-continued
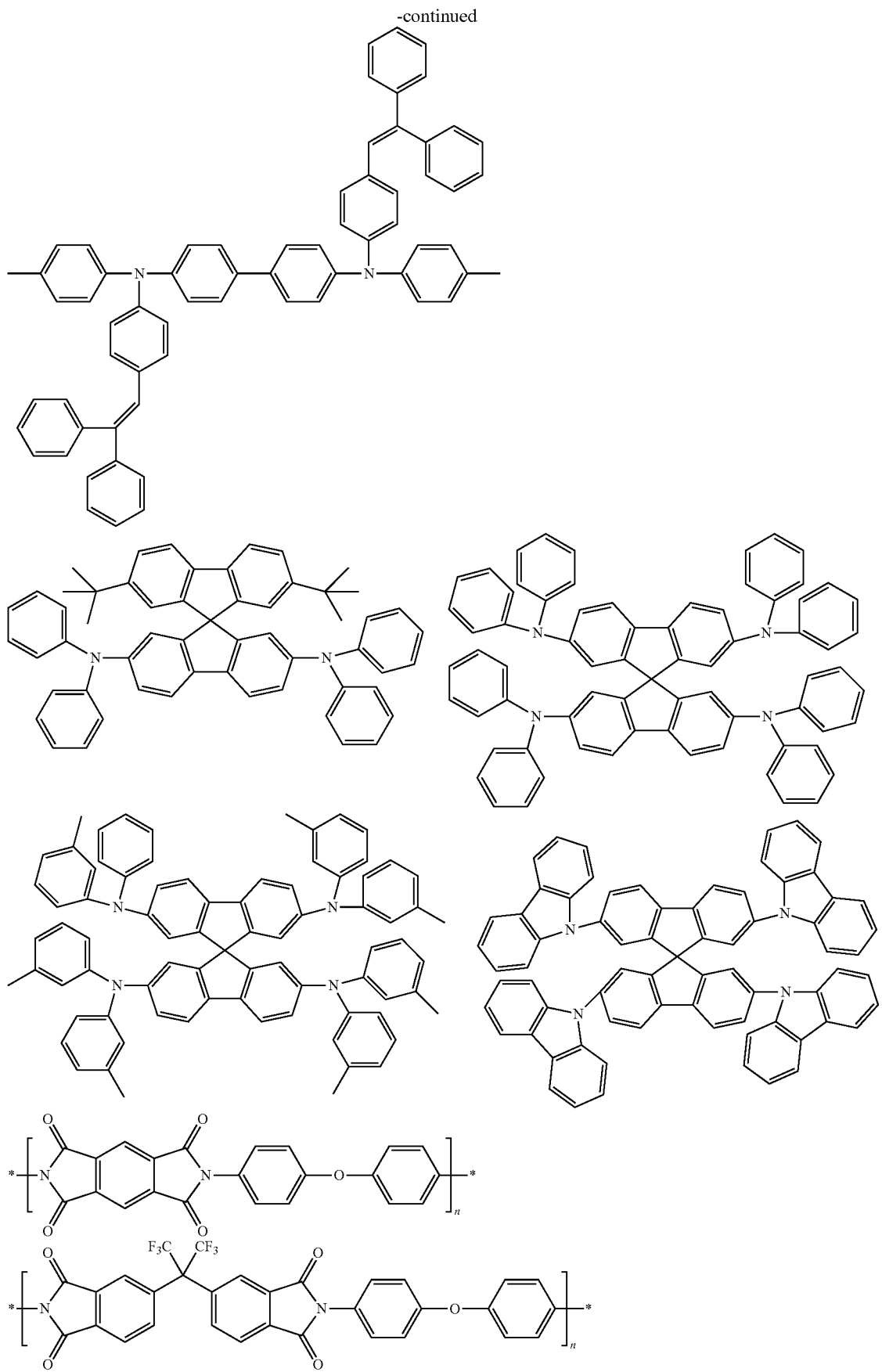

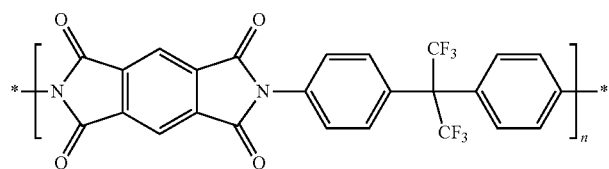
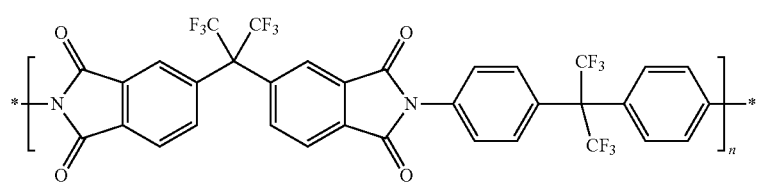
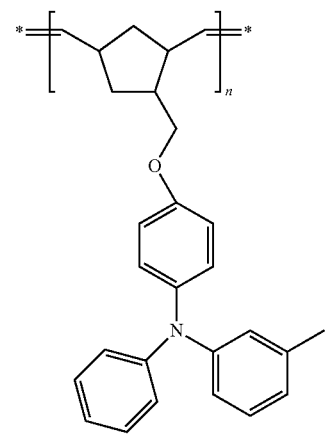
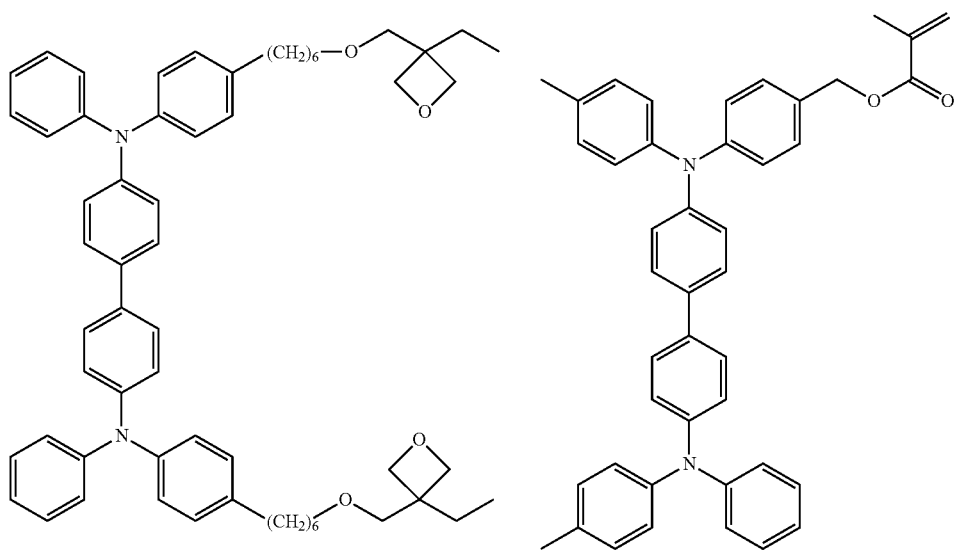

-continued
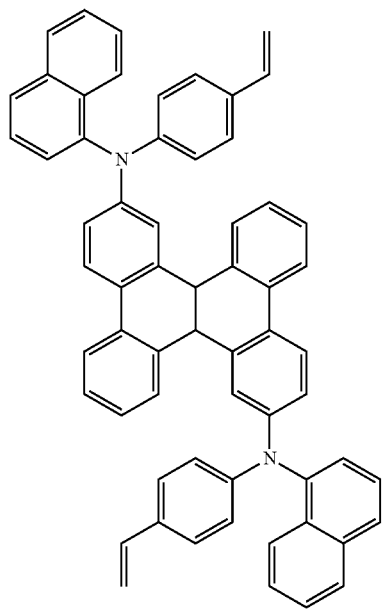
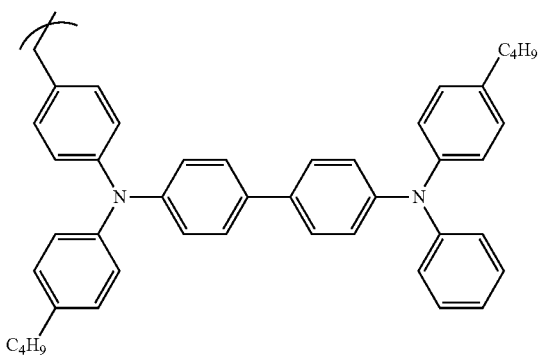
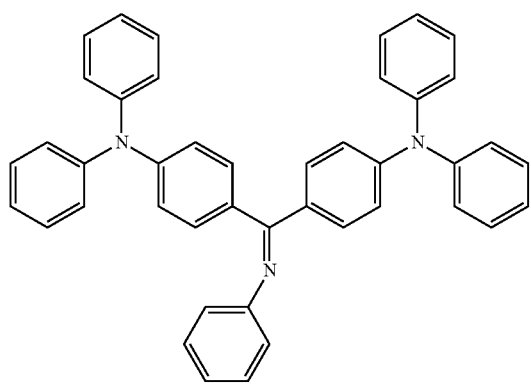
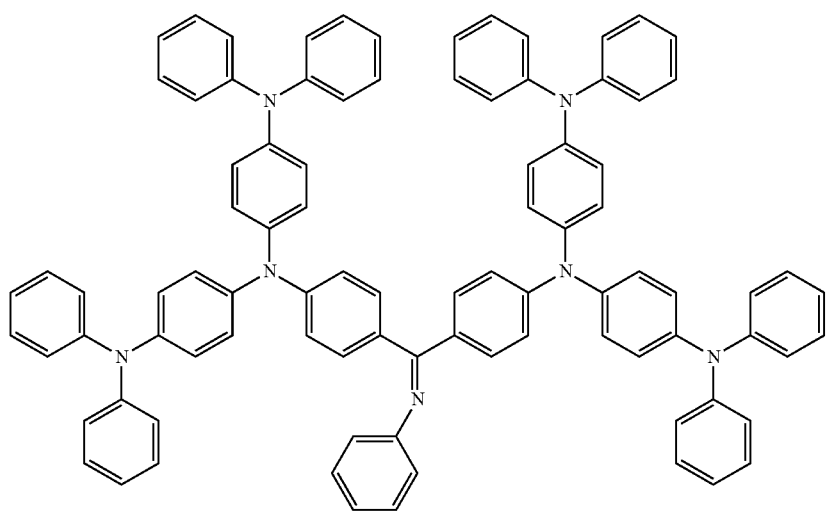

-continued
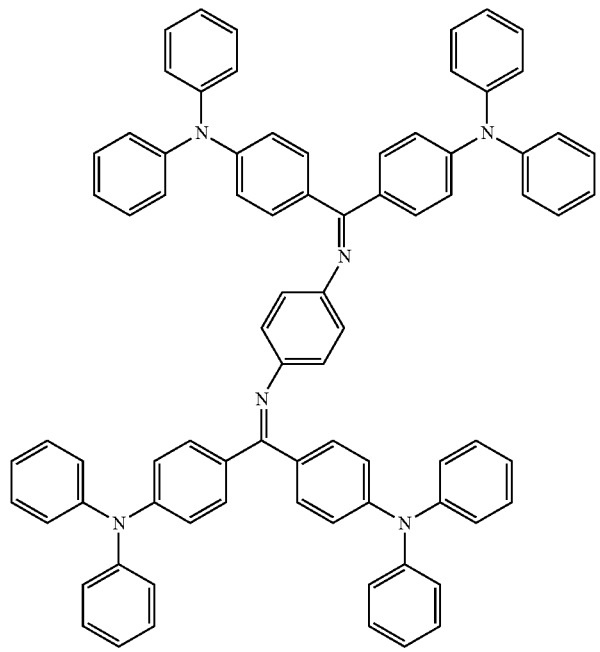
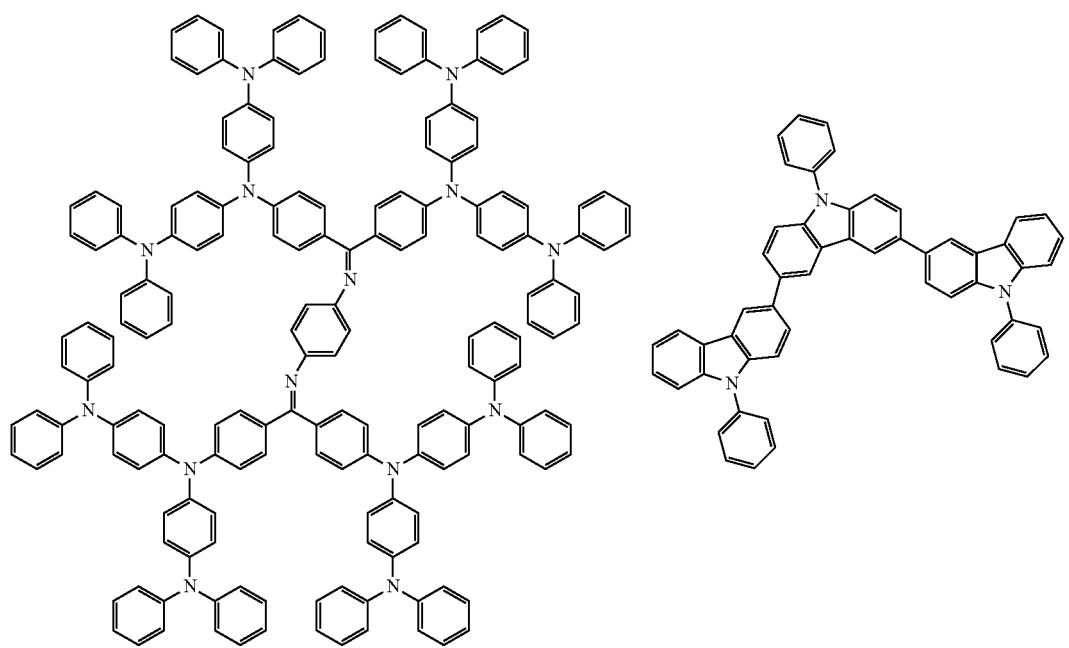 [SMILES: c1ccc(N(c2ccccc2)c2ccc(N(c3ccc(C(=Nc4ccc(N=C(c5ccc(N(c6ccc(N(c7ccccc7)c7ccccc7)cc6)c6ccc(N(c7ccccc7)c7ccccc7)cc6)cc5)c5ccc(N(c6ccc(N(c7ccccc7)c7ccccc7)cc6)c6ccc(N(c7ccccc7)c7ccccc7)cc6)cc5)cc4)c4ccc(N(c5ccc(N(c6ccccc6)c6ccccc6)cc5)c5ccc(N(c6ccccc6)c6ccccc6)cc5)cc4)cc3)c3ccc(N(c4ccccc4)c4ccccc4)cc3)cc2)cc1 ; c1ccc(-n2c3ccccc3c3cc(-c4ccc5c(c4)c4cc(-c6ccc7c(c6)c6ccccc6n7-c6ccccc6)ccc4n5-c4ccccc4)ccc32)cc1]

Preferred examples of a compound that may be used as the electron barrier material are shown below.
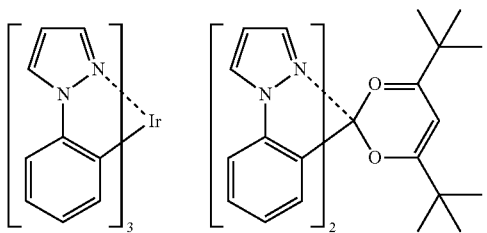
Preferred examples of a compound that may be used as the hole barrier material are shown below.
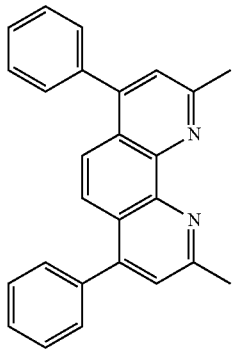
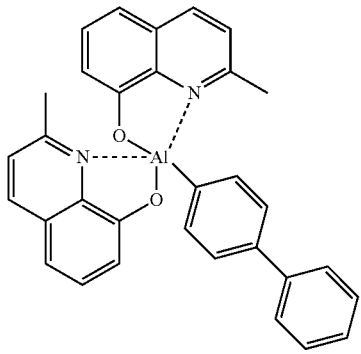
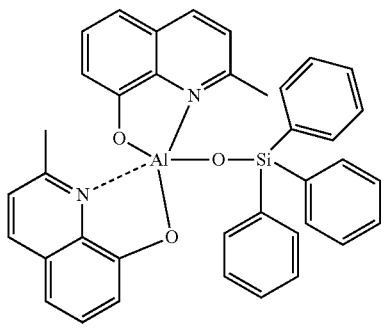
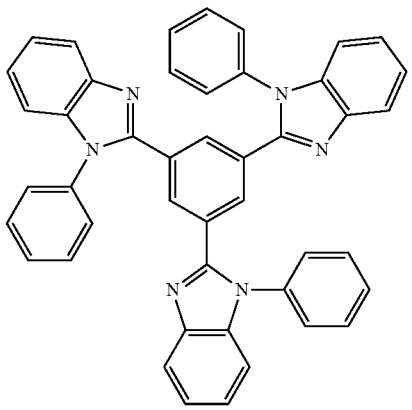
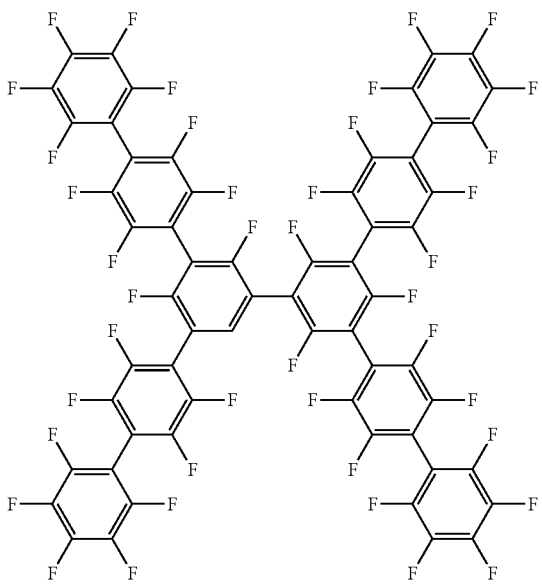
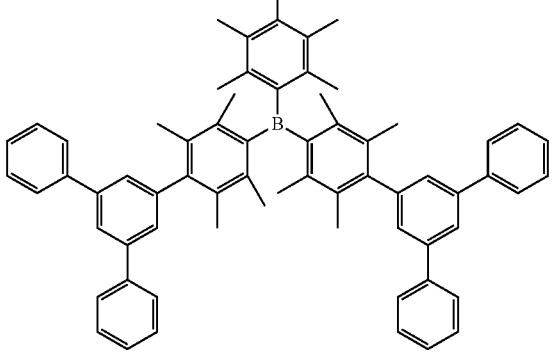

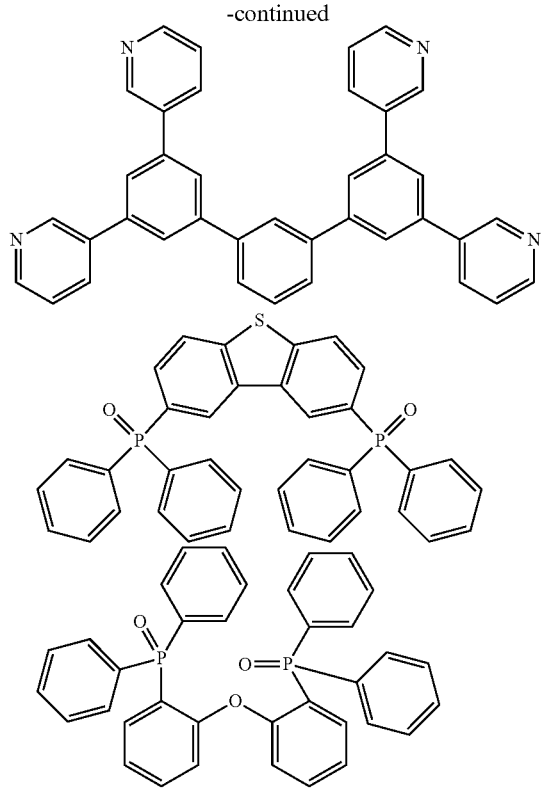
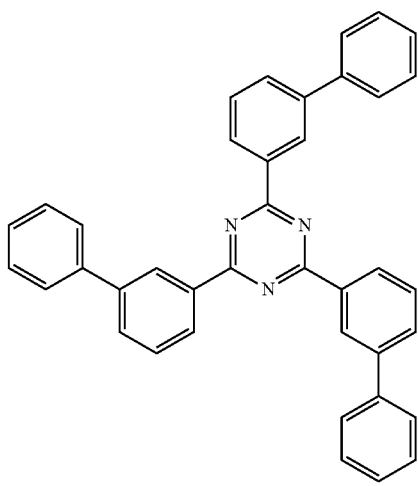
Preferred examples of a compound that may be used as the electron transporting material are shown below.
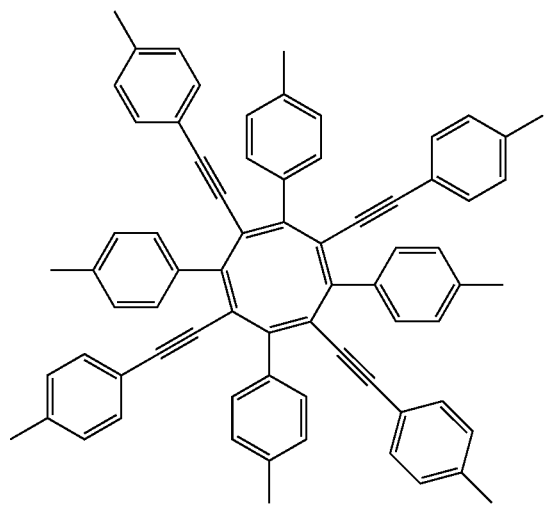
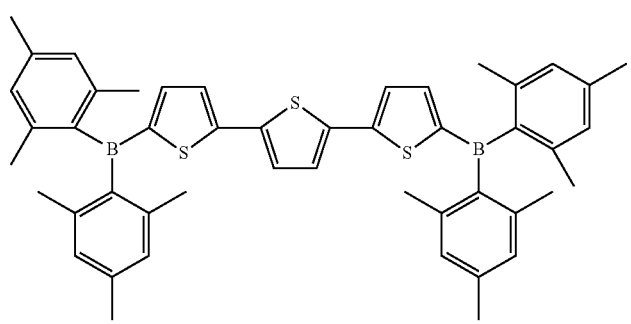
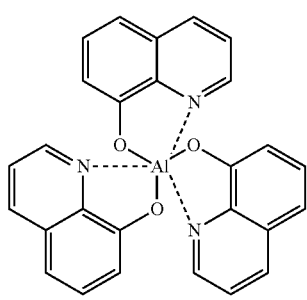

-continued
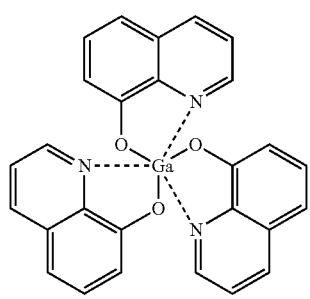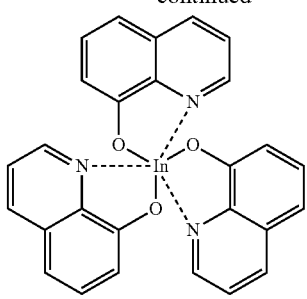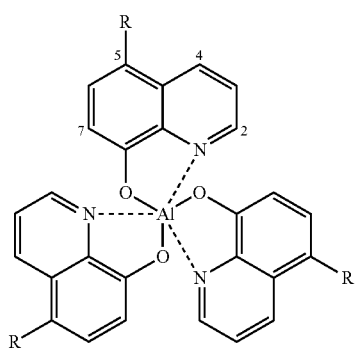
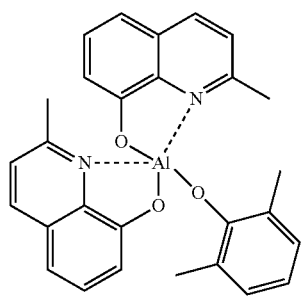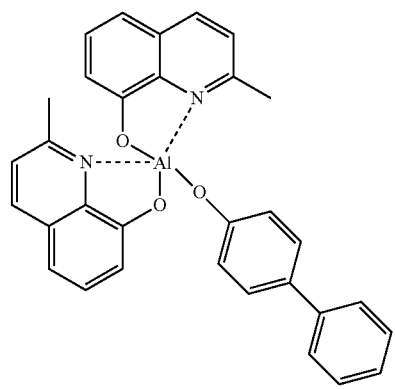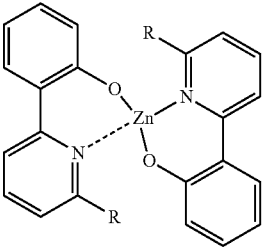
R =
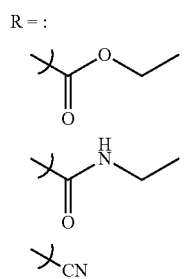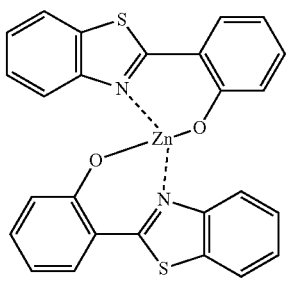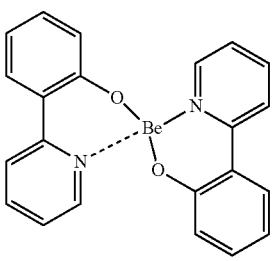
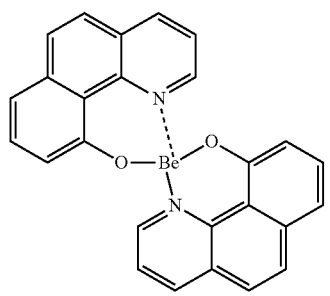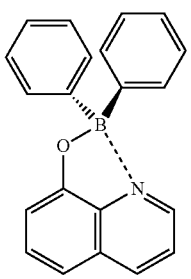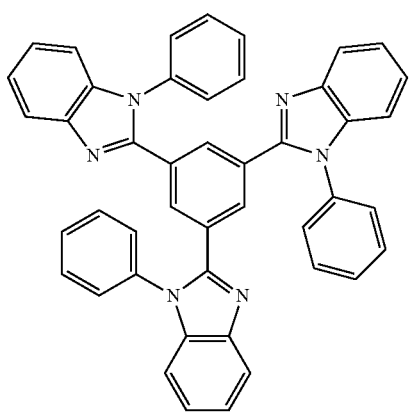

-continued
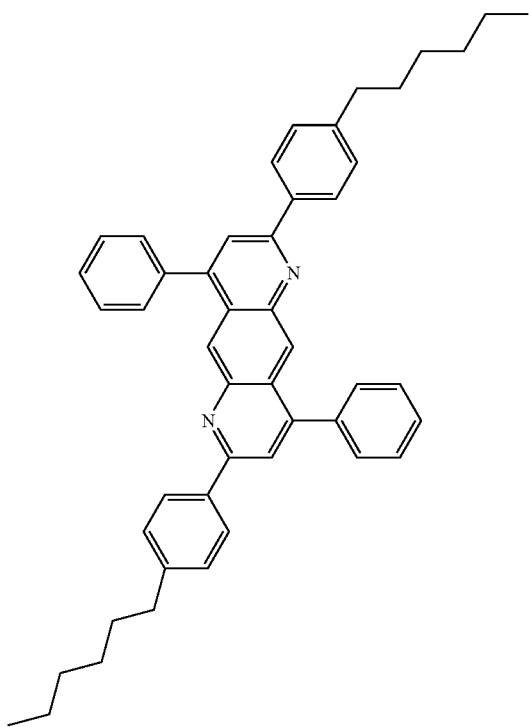
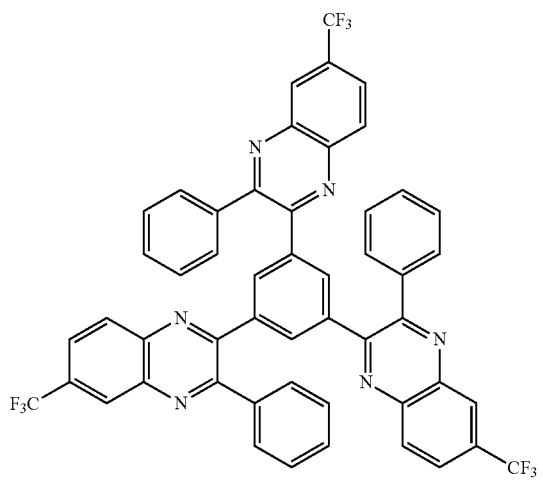
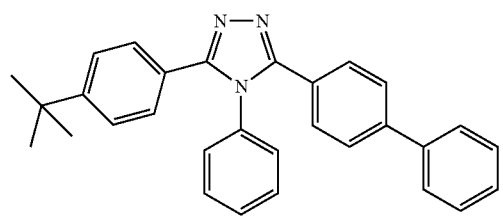
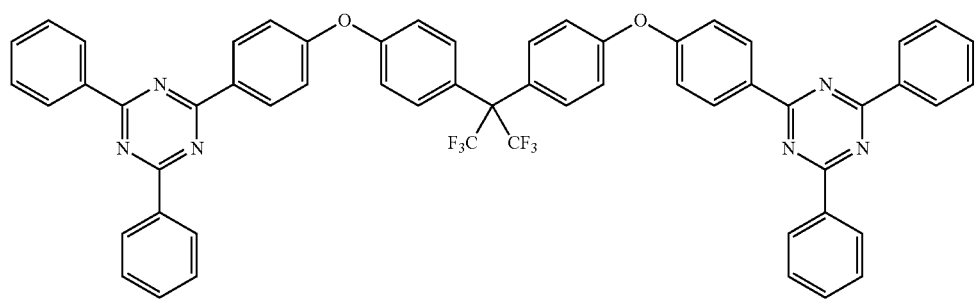
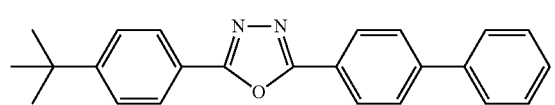

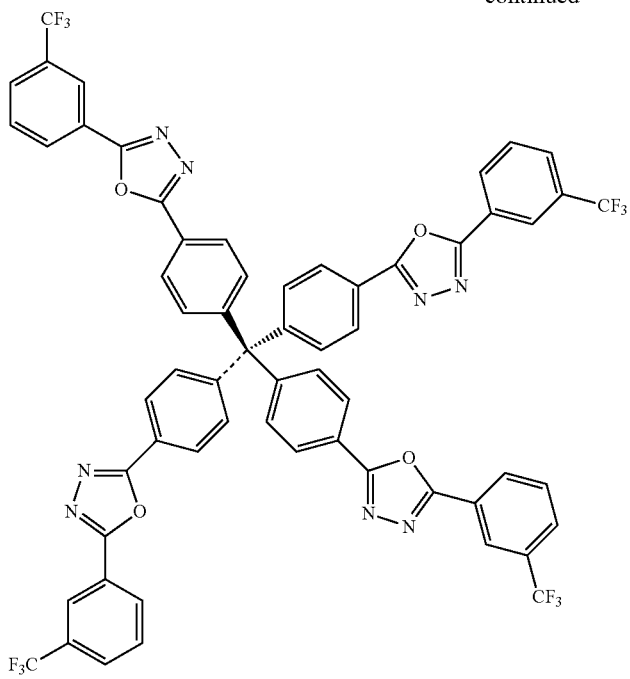
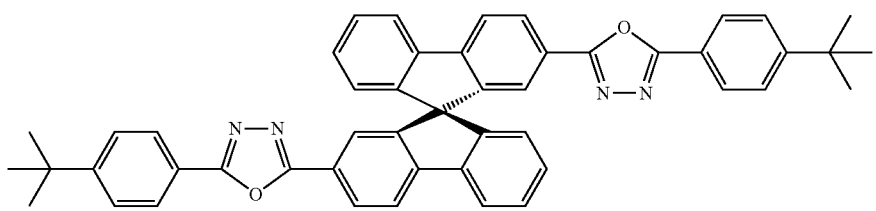
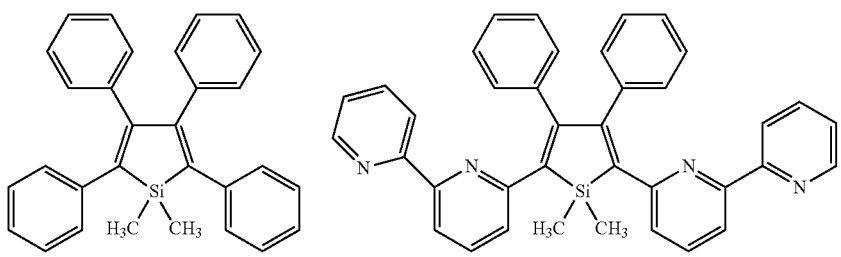
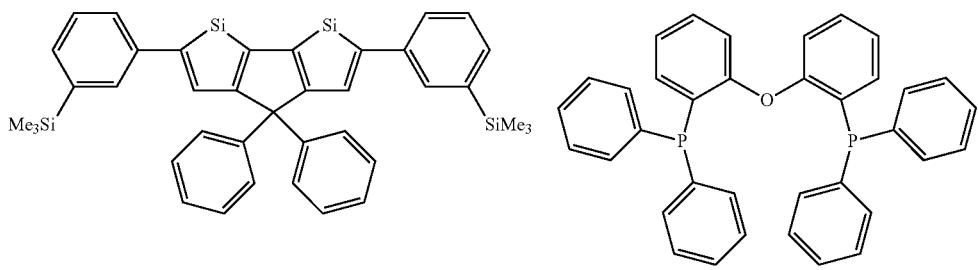
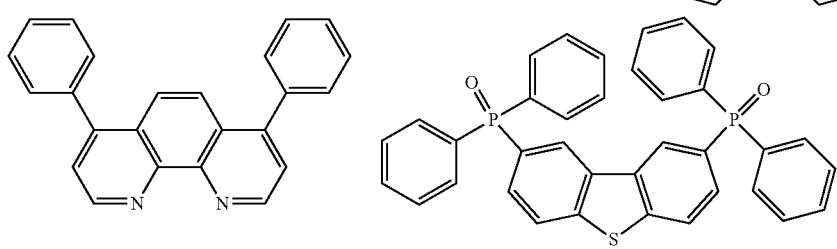

Preferred examples of a compound that may be used as the electron injection material are shown below.

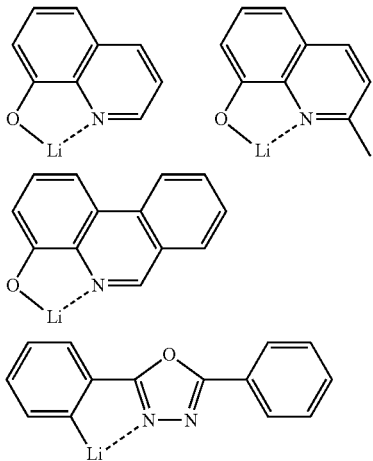

Preferred examples of a compound as a material that may be added are shown below. For example, the compound may be added as a stabilizing material.

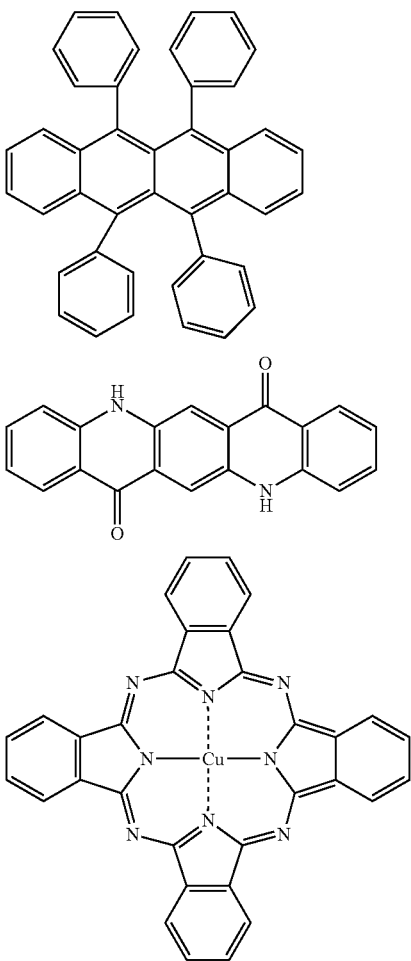

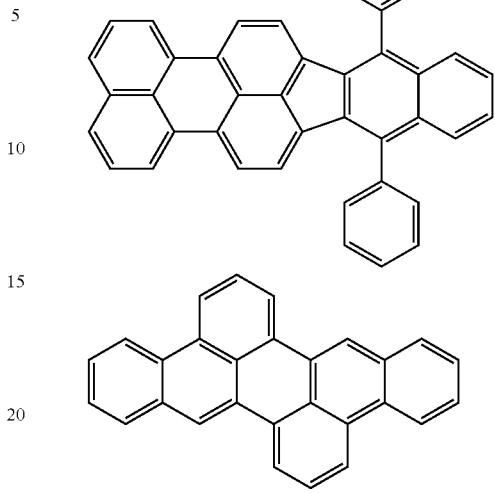

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X—Y matrix. According to the invention, an organic light emitting device that is largely improved in light emission efficiency may be obtained by adding the compound represented by the formula (1) in the light emitting layer. The organic light emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLES

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below.

Synthesis Example 1

Synthesis of Compound 1

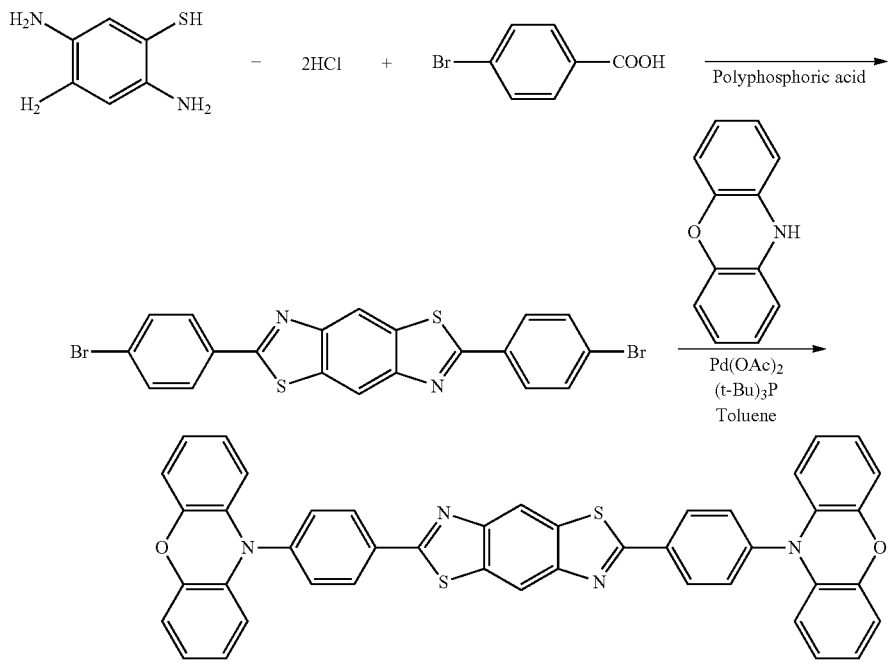

2.0 g (8.2 mmol) of 2,5-diaminobenzene-1,4-dithiol dihydrochloride and 3.8 g (18.8 mmol) of 4-bromobenzoic acid were placed in a 100 mL two-necked flask. 30 mL of polyphosphoric acid was added to the reactor, and the mixture was heated and stirred at 100° C. for 30 hours. After completing the reaction, the heating operation was terminated, and the reaction liquid was cooled to room temperature. Thereafter, the reaction product was placed in a mixed solution of 300 mL of water and 300 mL of chloroform. The organic layer and the aqueous layer were separated with a separating funnel, and the organic layer was dried and concentrated, to which 100 mL of methanol was then added to deposit a solid matter. The deposited product was suction-filtered and dried to provide 3.8 g of a dibrominated compound as a reaction intermediate in the form of yellow powder (yield: 93%).

Figure 2:
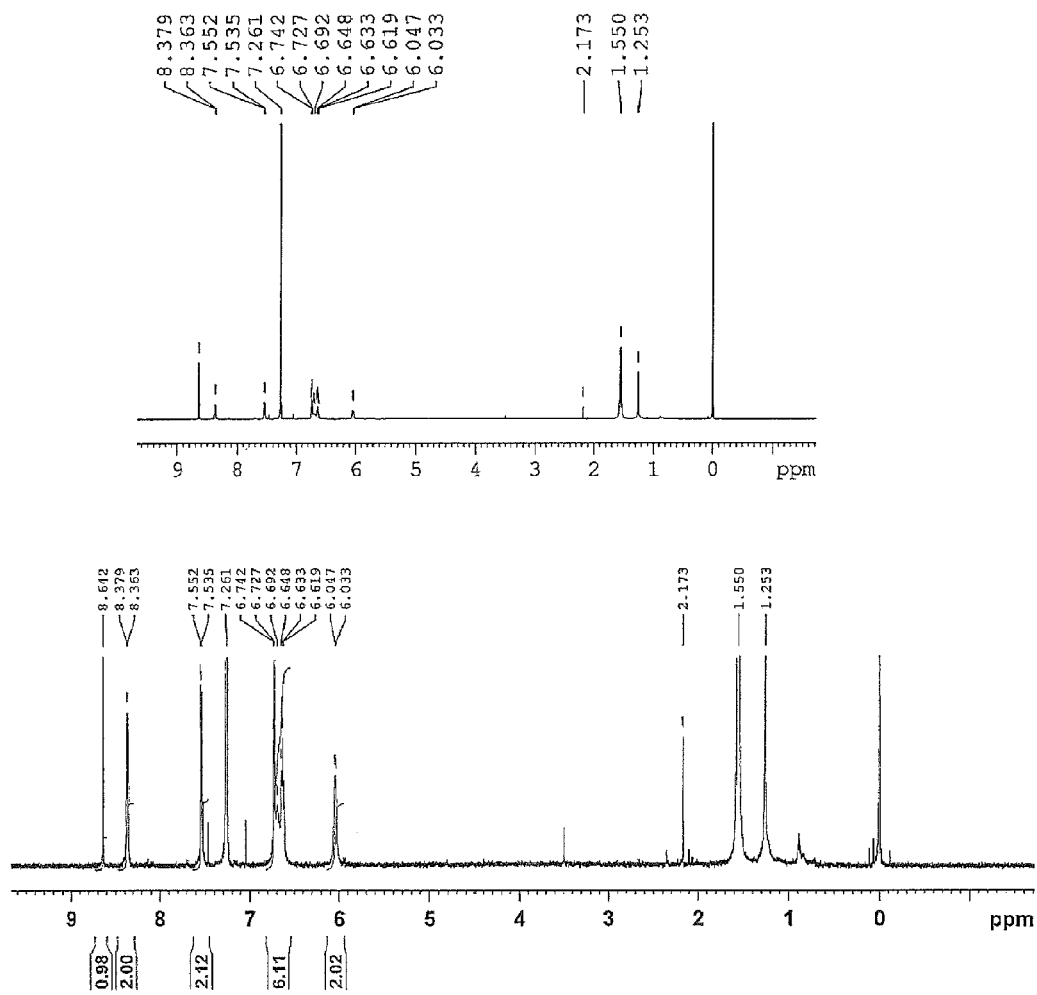
FIG. 2 is the $^1$H-NMR spectrum of the compound 1.
Figure 3:
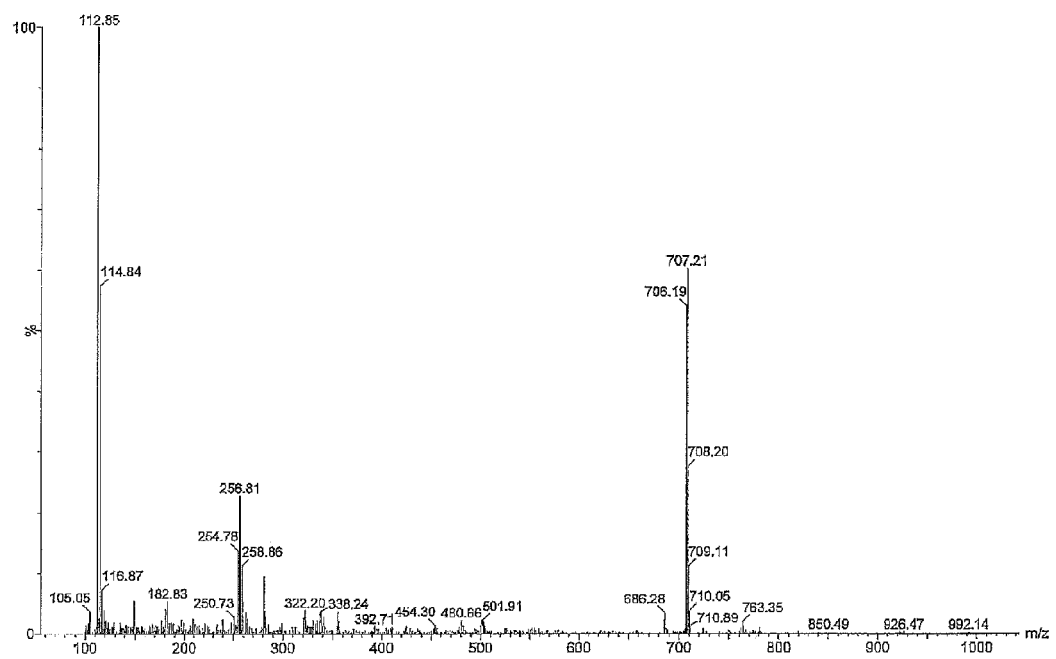
FIG. 3 is the mass spectrum of the compound 1.

A part of the resulting dibrominated compound which is in an amount of 0.71 g (1.4 mmol), 0.65 g (3.5 mmol) of phenoxazine and 0.59 g (4.3 mmol) of potassium carbonate were placed in a 50 mL two-necked flask having been replaced with nitrogen. A mixed liquid of 0.032 g (0.14 mmol) of palladium acetate and 0.029 g (0.14 mmol) of tri-tert-butylphosphine dissolved in 10 mL of dehydrated toluene having been deaerated with high purity nitrogen gas was added dropwise to the reactor, and the mixture was heated and stirred under a nitrogen atmosphere at 80° C. for 24 hours. After completing the reaction, 300 mL of water and 300 mL of chloroform were added to the reaction product, and the organic layer and the aqueous layer were separated. After concentrating the organic layer, 100 mL of methanol was added thereto, and the mixture was irradiated with ultrasonic wave for 10 minutes to deposit a solid matter. The deposited solid matter was suction-filtered and dried, and the resulting powder was purified by sublimation at 370° C. to provide 0.12 g of the compound 1 in the form of yellow powder (yield: 12%). FIG. 2 shows the $^1$H-NMR spectrum (CDCl$_3$, 500 MHz) thereof, and FIG. 3 shows the mass spectrum thereof.

Synthesis Example 2

Synthesis of Compound 3

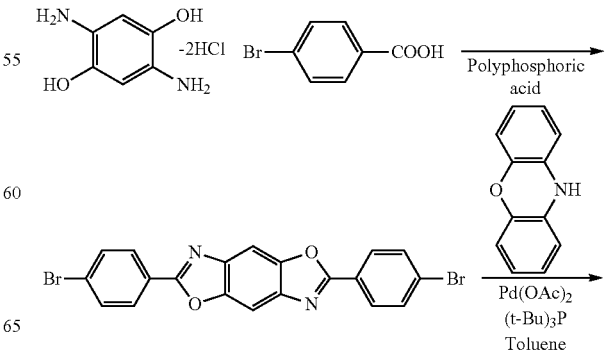

-continued

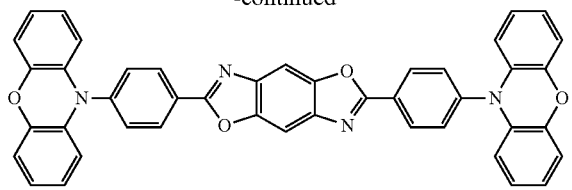

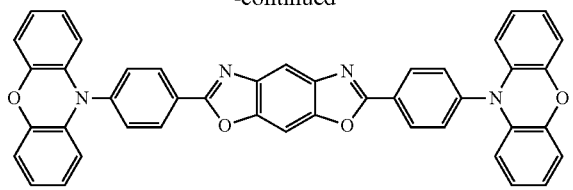

1.5 g (7.0 mmol) of 2,5-diaminohydroquinone dihydrochloride, 3.3 g (16.4 mmol) of 4-bromobenzoic acid and 30 mL of polyphosphoric acid were placed in a 100 mL two-necked flask, and the mixture was heated and stirred at 100° C. for 72 hours. After terminating the heating operation and cooling to room temperature, the reaction product was placed in a mixed solution of 300 mL of water and 300 mL of chloroform, and then the organic layer and the aqueous layer were separated with a separating funnel. The organic layer was dried and concentrated, to which 100 mL of methanol was then added to deposit a solid matter. The solid matter was filtered and dried to provide 2.7 g of a dibrominated compound as a reaction intermediate in the form of purple powder (yield: 79%).

A part of the resulting dibrominated compound which is in an amount of 0.70 g (1.5 mmol), 0.60 g (3.3 mmol) of phenoxazine and 1.23 g (9.9 mmol) of potassium carbonate were placed in a 200 mL two-necked flask having been replaced with nitrogen. 0.033 g (0.15 mmol) of palladium acetate and 0.030 g (0.15 mmol) of tri-tert-butylphosphine were dissolved in 50 mL of dehydrated toluene having been deaerated with high purity nitrogen gas and were added dropwise to the reactor, and the mixture was heated and stirred under a nitrogen atmosphere at 80° C. for 48 hours.

Figure 4:
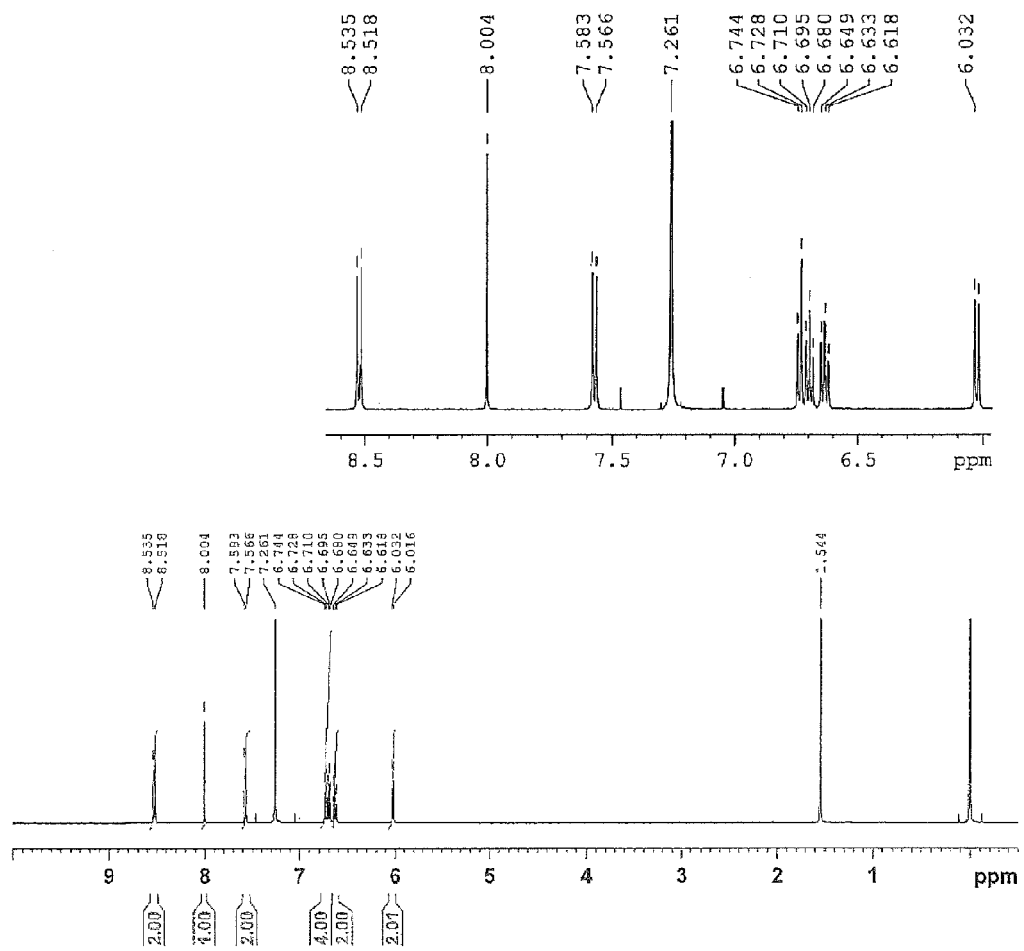
FIG. 4 is the $^1$H-NMR spectrum of the compound 3.
Figure 5:
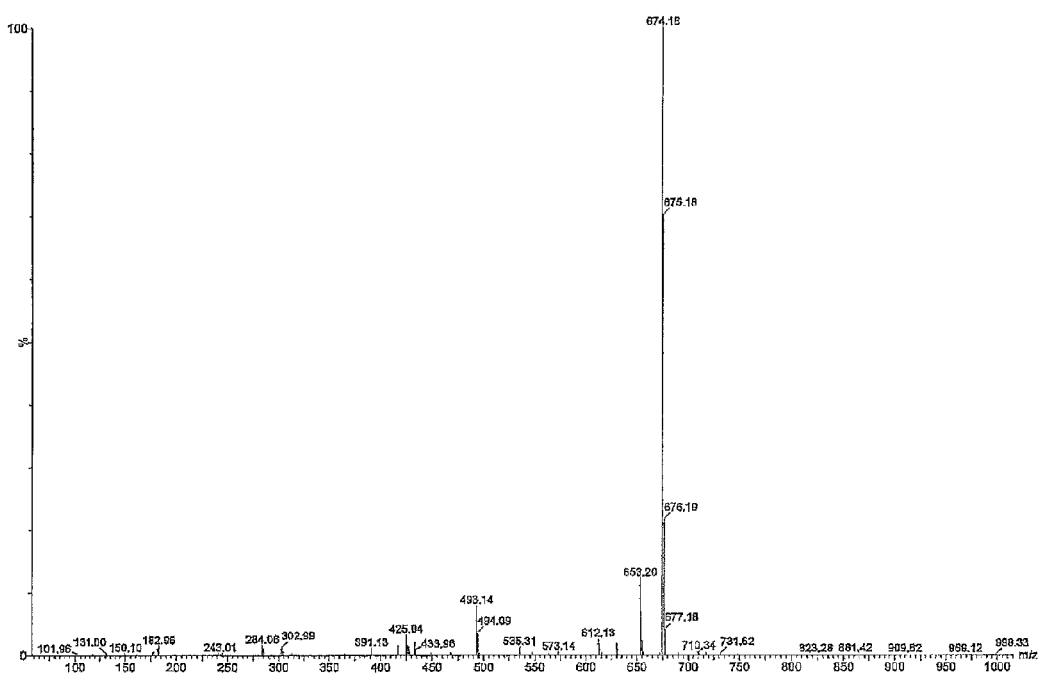
FIG. 5 is the mass spectrum of the compound 3.

After completing the reaction, the reaction product was placed in a mixed solution of 300 mL of water and 300 mL of chloroform, and the organic layer and the aqueous layer were separated with a separating funnel. After concentrating the organic layer to dryness, 100 mL of methanol was added thereto, and the mixture was irradiated with ultrasonic wave for 10 minutes to deposit a solid matter. The deposited solid matter was filtered and dried, and the resulting powder was purified by sublimation at 350° C. to provide 0.57 g of the compound 3 in the form of yellow acicular crystals (yield: 57%). FIG. 4 shows the $^1$H-NMR spectrum (CDCl$_3$, 500 MHz) thereof, and FIG. 5 shows the mass spectrum thereof.

Synthesis Example 3

Synthesis of Compound 4

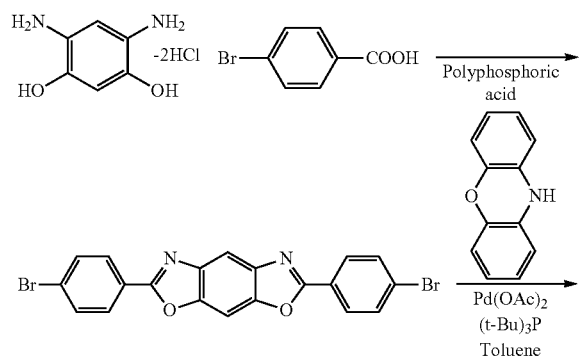

1.5 g (7.0 mmol) of 4,6-diaminoresorcinol dihydrochloride, 3.3 g (16.4 mmol) of 4-bromobenzoic acid and 20 mL of polyphosphoric acid were placed in a 100 mL two-necked flask, and the mixture was heated and stirred at 100° C. for 24 hours. After terminating the heating operation and cooling to room temperature, the reaction product was placed in a mixed solution of 300 mL of water and 300 mL of chloroform, and then the organic layer and the aqueous layer were separated with a separating funnel. The organic layer was dried and concentrated, to which 100 mL of methanol was then added to deposit a solid matter. The solid matter was filtered and dried to provide 3.0 g of a dibrominated compound as a reaction intermediate in the form of white powder (yield: 88%).

A part of the resulting dibrominated compound which is in an amount of 0.70 g (1.5 mmol), 0.60 g (3.3 mmol) of phenoxazine and 1.23 g (9.9 mmol) of potassium carbonate were placed in a 200 mL two-necked flask having been replaced with nitrogen. 0.033 g (0.15 mmol) of palladium acetate and 0.030 g (0.15 mmol) of tri-tert-butylphosphine were dissolved in 50 mL of dehydrated toluene having been deaerated with high purity nitrogen gas and were added dropwise to the reactor, and the mixture was heated and stirred under a nitrogen atmosphere at 80° C. for 48 hours.

Figure 6:
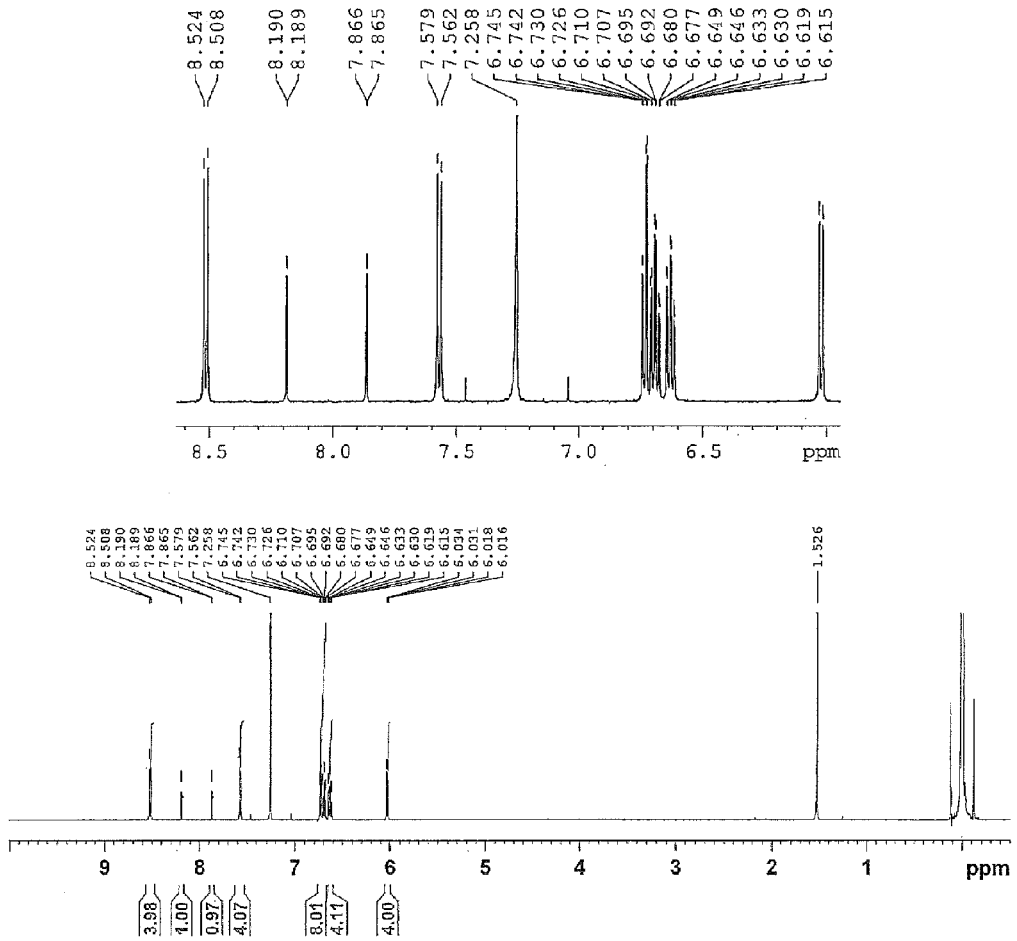
FIG. 6 is the $^1$H-NMR spectrum of the compound 4.
Figure 7:
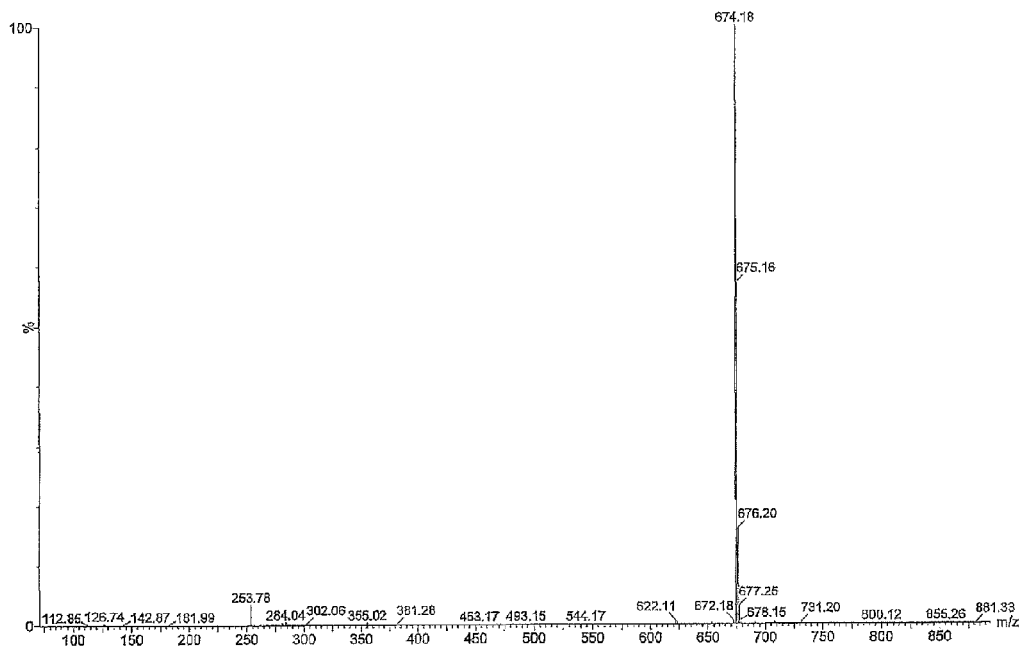
FIG. 7 is the mass spectrum of the compound 4.

After completing the reaction, the reaction product was placed in a mixed solution of 300 mL of water and 300 mL of chloroform, and the organic layer and the aqueous layer were separated with a separating funnel. After concentrating the organic layer to dryness, 100 mL of methanol was added thereto, and the mixture was irradiated with ultrasonic wave for 10 minutes to deposit a solid matter. The deposited solid matter was filtered and dried, and the resulting powder was purified by sublimation at 350° C. to provide 0.28 g of the compound 4 in the form of yellow acicular crystals (yield: 28%). FIG. 6 shows the $^1$H-NMR spectrum (CDCl$_3$, 500 MHz) thereof, and FIG. 7 shows the mass spectrum thereof.

Example 1

Production and Evaluation of Organic Photoluminescent Device (Thin Film)

The compound 1 and CBP were vapor-deposited on a silicon substrate from separate vapor deposition sources under a condition of a vacuum degree of 5.0×10$^{-4}$ Pa to form a thin film having a thickness of 100 nm and a concentration of the compound 1 of 6.0% by weight at a rate of 0.3 nm/sec, thereby producing an organic photoluminescent device.

Figure 8:
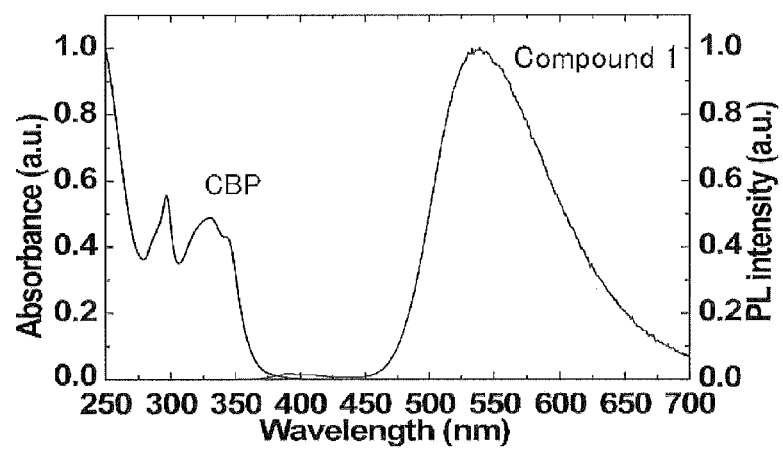
FIG. 8 is the light emission spectrum of the organic photoluminescent device using the compound 1.
Figure 9:
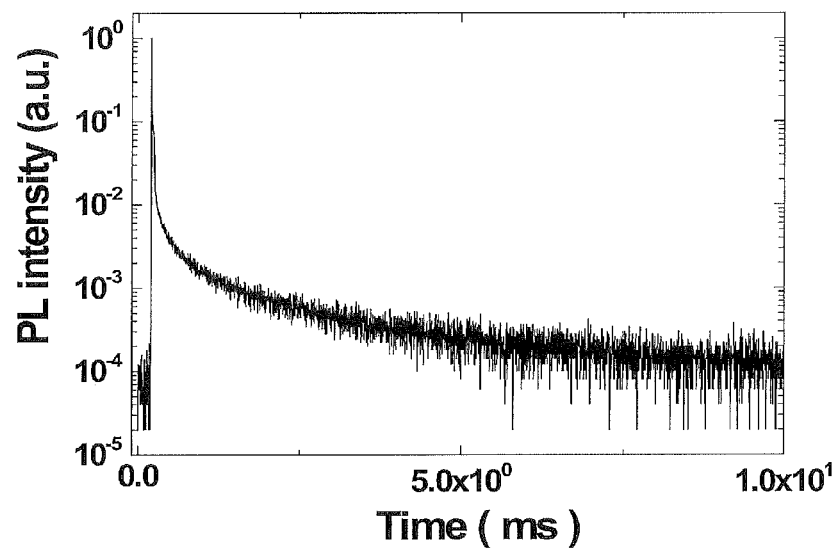
FIG. 9 is the transient decay curve of the organic photoluminescent device using the compound 1.

The organic photoluminescent device thus produced was measured with Semiconductor Parameter Analyzer (E5273A, produced by Agilent Technologies, Inc.), Optical Power Meter (1930C, produced by Newport Corporation), Optic Spectrometer (USB2000, produced by Ocean Optics, Inc.) and Streak Camera (Model C4334, produced by Hamamatsu Photonics K.K.). FIG. 8 shows the light emission spectrum thereof with excitation light having a wavelength of 330 nm, and FIG. 9 shows the transient decay curve thereof. The transient decay curve shows the measurement result of the light emission lifetime obtained by measuring the process where the light emission intensity is deactivated on irradiating the compound with excitation light. In ordinary one-component light emission (fluorescent light or phosphorescent light), the light emission intensity is decays monoexponentially. This means that the light emission intensity decays linearly on a graph with the semilogarithm as the ordinate. In a transient decay curve of the compound 1, while a linear component (fluorescent light) was observed in the initial stage of observation, a component that deviated from the linearity appeared after several microseconds. The later component is light emission of the delayed component, and the signal thereof added to the initial component appears as a long tail curve on the longer time side. Thus, the measurement of the light emission lifetime revealed that the compound 1 was a light emitter that contained a delayed component in addition to a fluorescent component.

The photoluminescence quantum efficiency measured at 300 K was 60% in the air and 78% in a nitrogen atmosphere.

Figure 10:
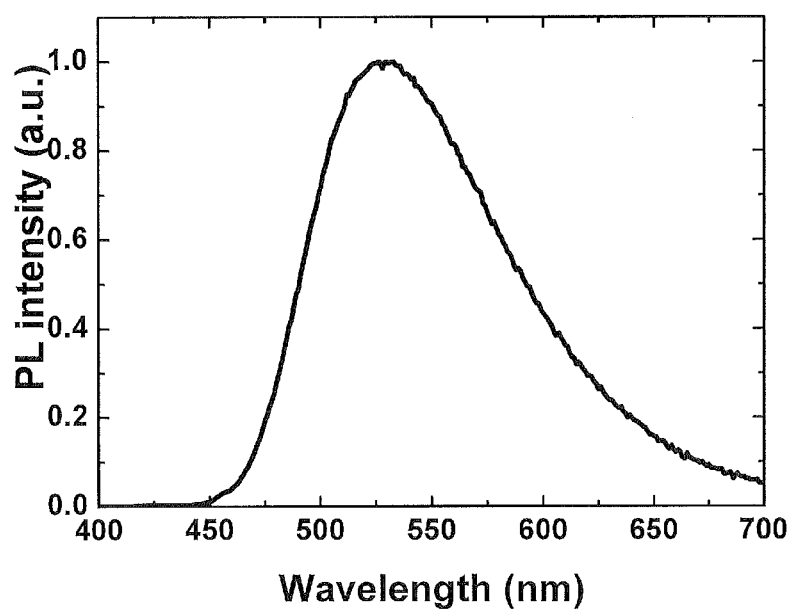
FIG. 10 is the light emission spectrum of the organic photoluminescent device using the compound 3.
Figure 11:
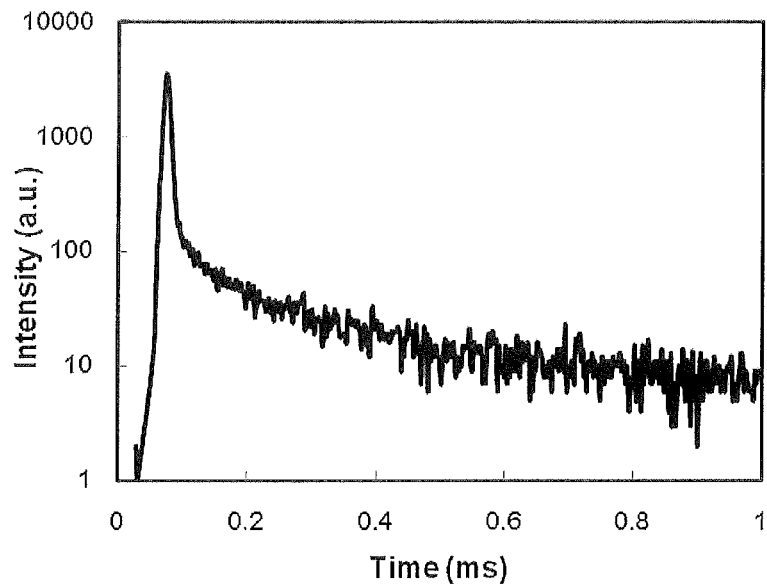
FIG. 11 is the transient decay curve of the organic photoluminescent device using the compound 3.

An organic photoluminescent device was produced in the same manner except that the compound 3 was used instead of the compound 1. FIG. 10 shows the light emission spectrum thereof with excitation light having a wavelength of 330 nm, and FIG. 11 shows the transient decay curve thereof. The photoluminescence quantum efficiency measured at 300 K was 21% in the air and 60% in a nitrogen atmosphere.

Figure 12:
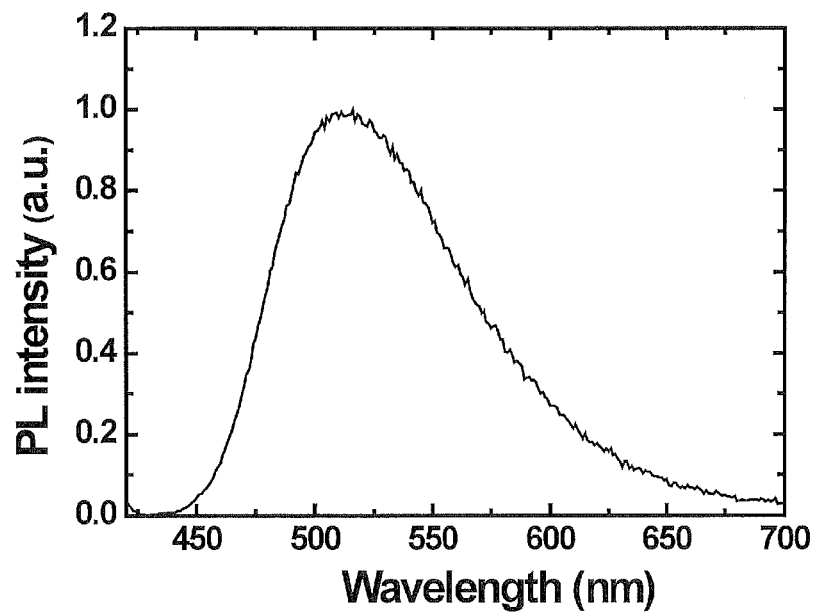
FIG. 12 is the light emission spectrum of the organic photoluminescent device using the compound 4.
Figure 13:
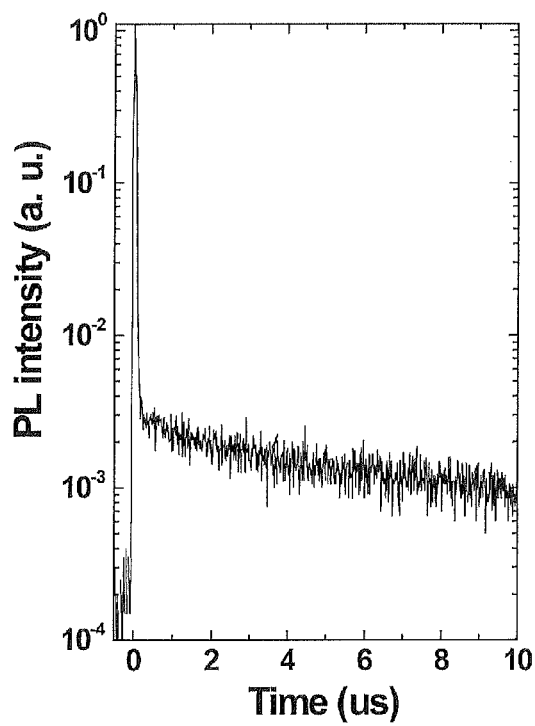
FIG. 13 is the transient decay curve of the organic photoluminescent device using the compound 4.

An organic photoluminescent device was produced in the same manner except that the compound 4 was used instead of the compound 1. FIG. 12 shows the light emission spectrum thereof with excitation light having a wavelength of 330 nm, and FIG. 13 shows the transient decay curve thereof. The photoluminescence quantum efficiency measured at 300 K was 84% in the air and 98% in a nitrogen atmosphere.

Example 2

Production and Evaluation of Organic Electroluminescent Device

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, α-NPD was formed to a thickness of 35 nm on ITO, and thereon the compound 1 and CBP were co-deposited from separate vapor deposition sources to form a layer having a thickness of 15 nm, which was designated as a light emitting layer. At this time, the concentration of the compound 1 was 6.0% by weight. TPBi was then formed to a thickness of 65 nm, then lithium fluoride (LiF) was vapor-deposited to a thickness of 0.8 nm, and then aluminum (Al) was vapor-deposited to a thickness of 80 nm to form a cathode, thereby producing an organic electroluminescent device.

Figure 14:
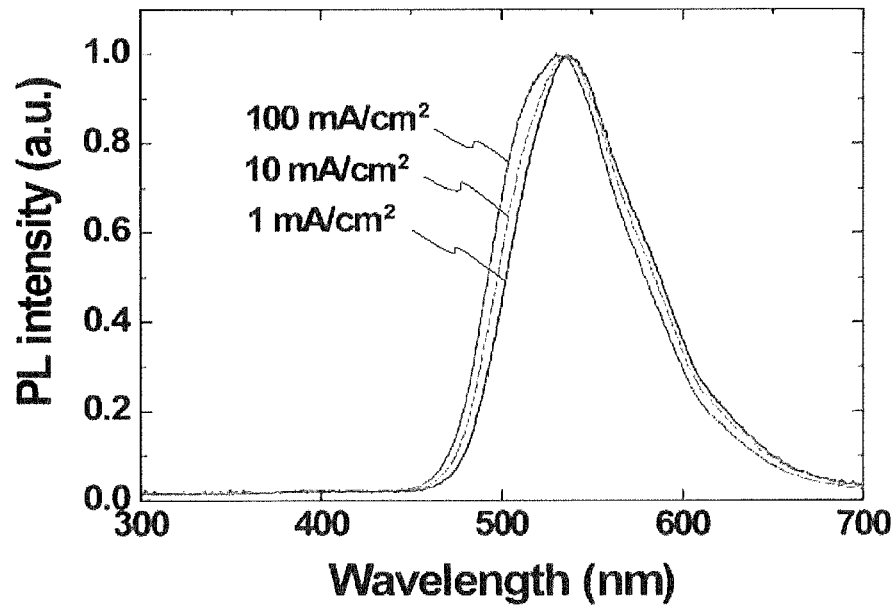
FIG. 14 is the light emission spectra of the organic electroluminescent device using the compound 1.
Figure 15:
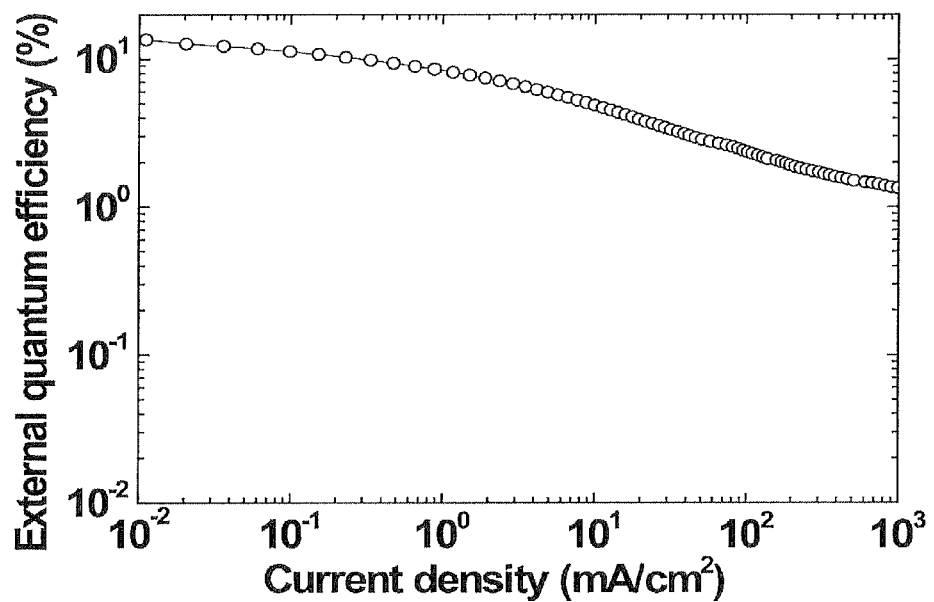
FIG. 15 is a graph showing the electric current density-external quantum efficiency characteristics of the organic electroluminescent device using the compound 1.

The organic electroluminescent device thus produced was measured with Semiconductor Parameter Analyzer (E5273A, produced by Agilent Technologies, Inc.), Optical Power Meter (1930C, produced by Newport Corporation) and Optic Spectrometer (USB2000, produced by Ocean Optics, Inc.). FIG. 14 shows the light emission spectra thereof, and FIG. 15 shows the electric current density-external quantum efficiency characteristics thereof. The organic electroluminescent device using the compound 1 as a light emitter achieved a high external quantum efficiency of 13.5%. As the photoluminescence quantum efficiency using the compound 1 as a light emitter was 78%, the single exciton formation probability was calculated as 87% (assuming that the light extraction efficiency was 20%, and the recombination probability was 1000).

If an ideally balanced organic electroluminescent device is produced with a fluorescent emitter having a light emission quantum efficiency of 100%, the external quantum efficiency of fluorescent light emission of the device may be from 5 to 7.5% assuming that the light extraction efficiency is from 20 to 30%. It has been ordinarily considered that the value is the theoretical limit value of an external quantum efficiency of an organic electroluminescent device using a fluorescent emitter. The organic electroluminescent device using the compound 1 of the invention is considerably excellent in such a point that a high external quantum efficiency (13.5%) that exceeds the theoretical limit value is achieved.

Figure 16:
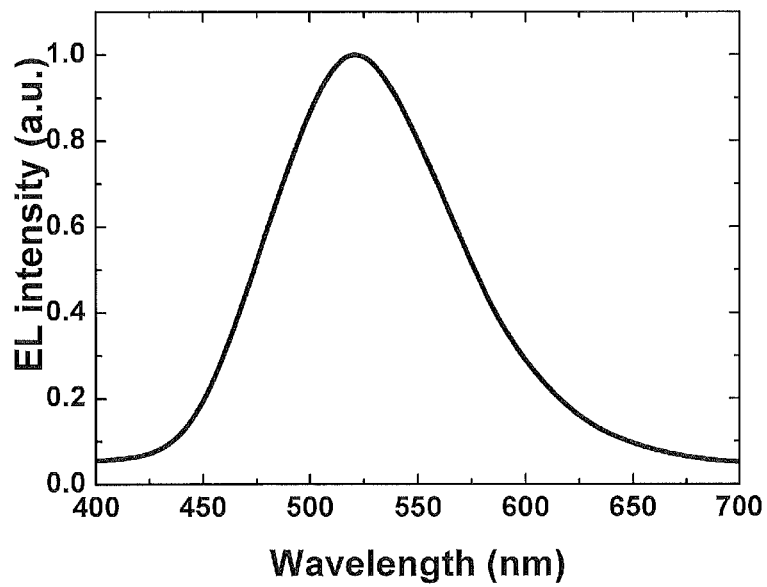
FIG. 16 is the light emission spectrum of the organic electroluminescent device using the compound 3.
Figure 17:
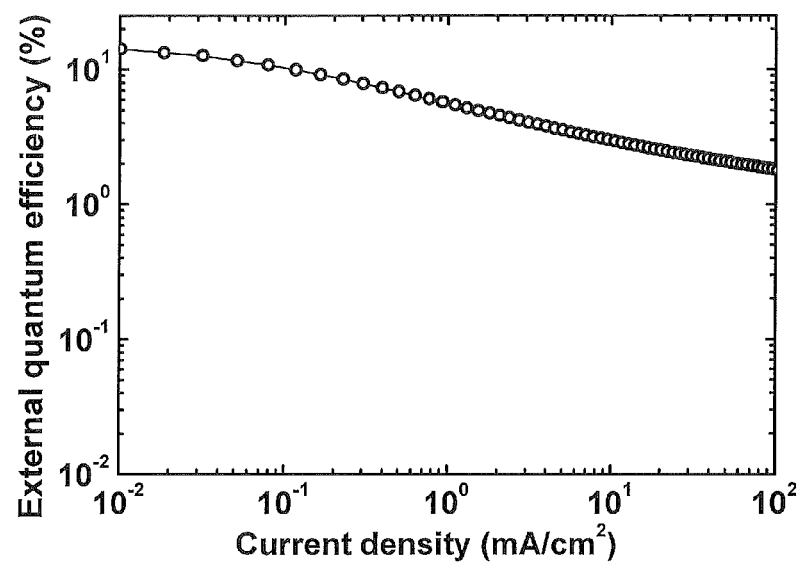
FIG. 17 is a graph showing the electric current density-external quantum efficiency characteristics of the organic electroluminescent device using the compound 3.

An organic electroluminescent device was produced in the same manner except that the compound 3 was used instead of the compound 1, and mCBP was used instead of CBP. FIG. 16 shows the light emission spectra thereof, and FIG. 17 shows the electric current density-external quantum efficiency characteristics thereof. The organic electroluminescent device using the compound 3 as a light emitter achieved a high external quantum efficiency of 13.3%. As the photoluminescence quantum efficiency using the compound 3 as a light emitter was 81%, the single exciton formation probability was calculated as 82% (assuming that the light extraction efficiency was 20%, and the recombination probability was 100%).

Figure 18:
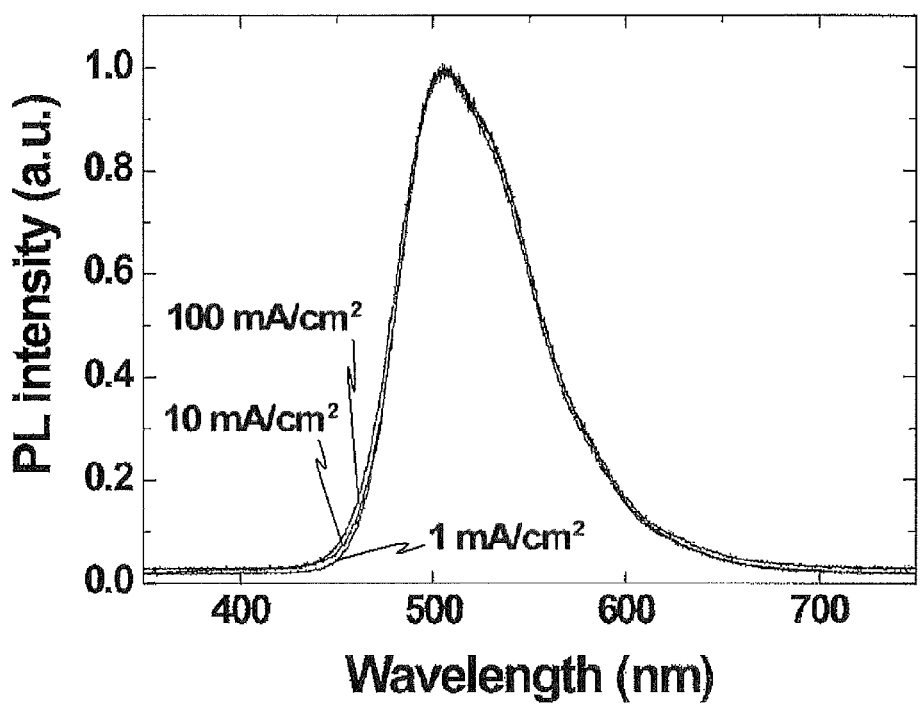
FIG. 18 is the light emission spectra of the organic electroluminescent device using the compound 4.
Figure 19:
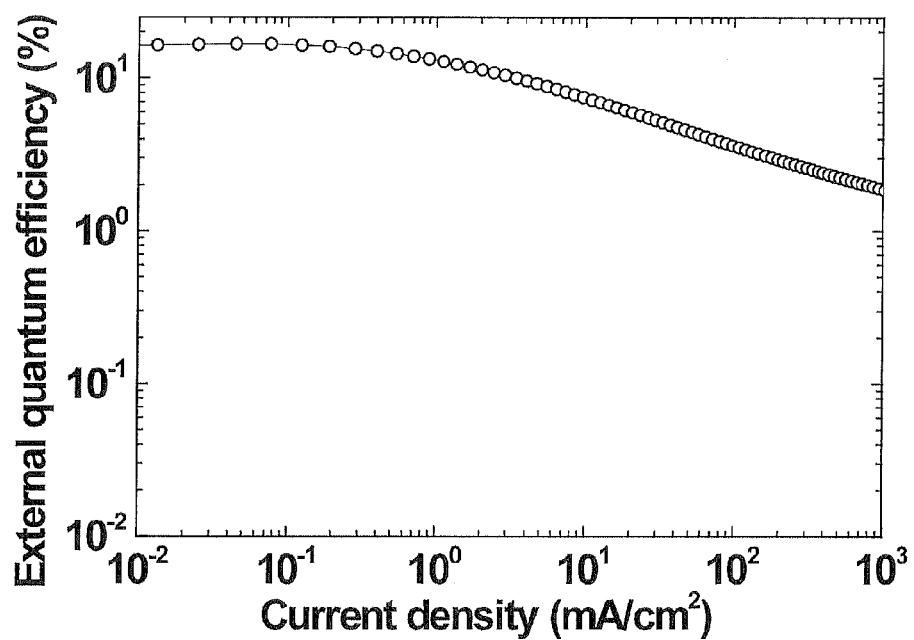
FIG. 19 is a graph showing the electric current density-external quantum efficiency characteristics of the organic electroluminescent device using the compound 4.

An organic electroluminescent device was produced in the same manner except that the compound 4 was used instead of the compound 1, and mCBP was used instead of CBP. FIG. 18 shows the light emission spectra thereof, and FIG. 19 shows the electric current density-external quantum efficiency characteristics thereof. The organic electroluminescent device using the compound 4 as a light emitter achieved a high external quantum efficiency of 16.4%. As the photoluminescence quantum efficiency using the compound 4 as a light emitter was 98%, the single exciton formation probability was calculated as 84% (assuming that the light extraction efficiency was 20%, and the recombination probability was 100%).

The difference between the singlet energy and the triplet energy of the molecule ($\Delta E_{ST}$) was calculated for the compound A having the aforementioned structure and the compounds 1, 3 and 4 in Examples by the density-functional formalism (TD-DFT (PBE1PBE/6-31G). The results are shown in Table 1. The results revealed that the compound A had a larger $\Delta E_{ST}$ value than the compounds of Examples and thus clearly had a lower light emission capability.

TABLE 1

| | $\Delta E_{ST}$ |
| --- | --- |
| Compound A | 0.77 |
| Compound 1 | 0.13 |
| Compound 3 | 0.14 |
| Compound 4 | 0.12 |

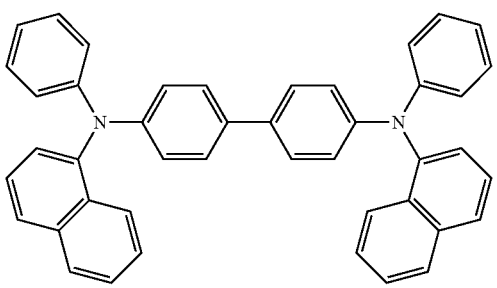

α-NPD

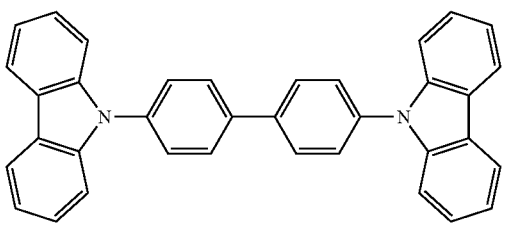

CBP

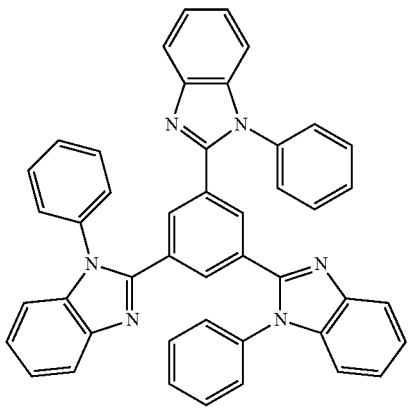

TPBi

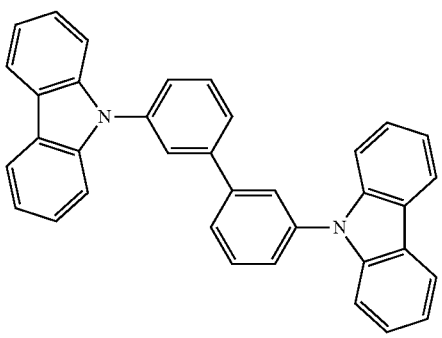

mCBP

INDUSTRIAL APPLICABILITY

The compound of the invention is useful as a light emitter. Accordingly, the compound of the invention may be effectively used as a light emitter of an organic light emitting device, such as an organic electroluminescent device. The compound of the invention includes a compound that emits delayed fluorescent light, and thus may be capable of providing an organic light emitting device having a high light emission efficiency. Thus, the invention has high industrial applicability.

REFERENCE SIGNS LIST 1 substrate
2 anode
3 hole injection layer
4 hole transporting layer
5 light emitting layer
6 electron transporting layer
7 cathode

What is claimed is:
1. A compound represented by the following Formula (1):

D-A-D      Formula (1)

wherein:

A represents a divalent group having a structure represented by one of the following Formulae (2) to (5):

Formula (2)

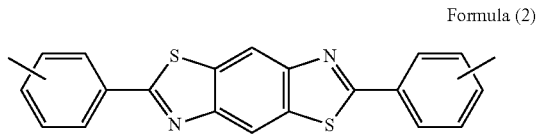

Formula (3)

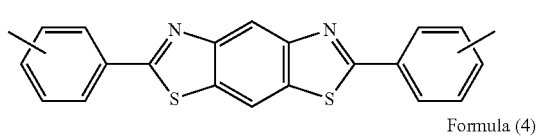

Formula (4)

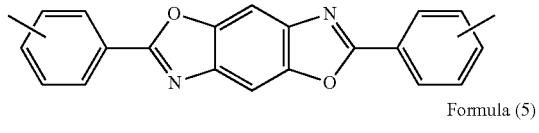

Formula (5)

in which a hydrogen atom in the structures of the Formulae (2) to (5) may be substituted by a substituent; and the two groups of D each independently represent a group having a structure selected from the following structures:

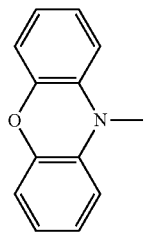 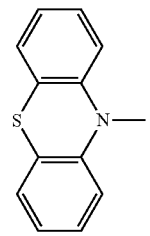

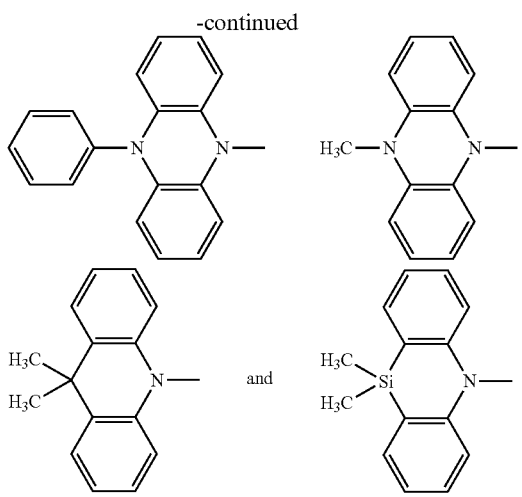

in which a hydrogen atom in the above structures may be substituted by a substituent.

2. The compound according to claim 1, wherein A in the Formula (1) has a structure represented by one of the following Formulae (6) to (9):

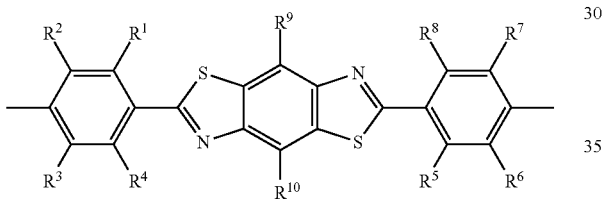

Formula (6)

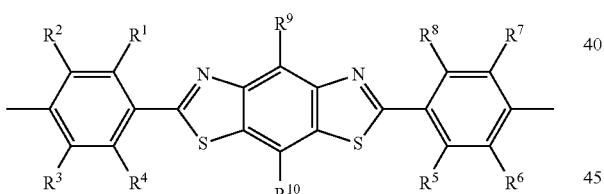

Formula (7)

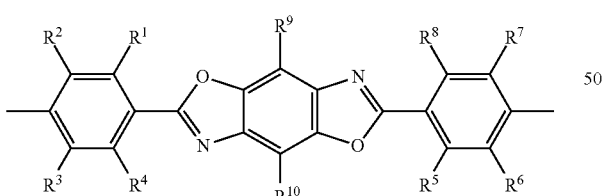

Formula (8)

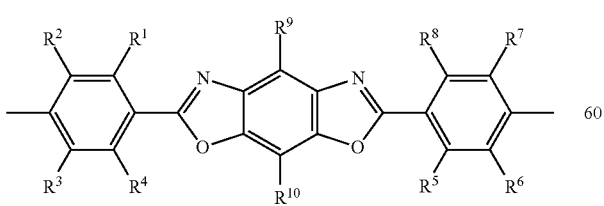

Formula (9)

in which $R^1$ to $R^{10}$ in the formulae (6) to (9) each independently represent a hydrogen atom or a substituent, and $R^1$ and $R^2$, $R^3$ and $R^4$, $R^5$ and $R^6$, and $R^7$ and $R^8$ each may be bonded to each other to form a cyclic structure.

3. The compound according to claim 1, wherein the two groups of D have the same structure.

4. The compound according to claim 1, wherein D in the Formula (1) has a structure represented by one of the following Formulae (10) to (12):

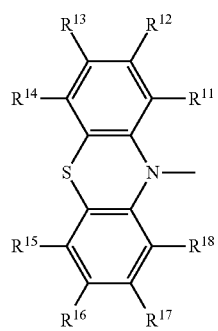

Formula (10)

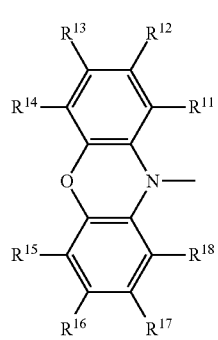

Formula (11)

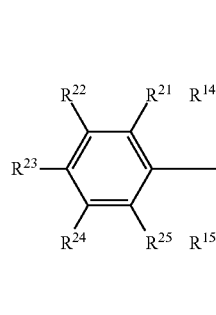

Formula (12)

in which $R^{11}$ to $R^{18}$ and $R^{21}$ to $R^{25}$ in the Formulae (10) to (12) each independently represent a hydrogen atom or a substituent, and $R^{11}$ and $R^{12}$, $R^{12}$ and $R^{13}$, $R^{13}$ and $R^{14}$, $R^{15}$ and $R^{16}$, $R^{16}$ and $R^{17}$, $R^{17}$ and $R^{18}$, $R^{21}$ and $R^{22}$, $R^{22}$ and $R^{23}$, $R^{23}$ and $R^{24}$, and $R^{24}$ and $R^{25}$ each may be bonded to each other to form a cyclic structure.

5. The compound according to claim 4, wherein D has a structure represented by the Formula (11).

6. A light emitter consisting of a compound represented by the following Formula (1):

D-A-D     Formula (1)

wherein:

A represents a divalent group having a structure represented by one of the following Formulae (2) to (5):

81

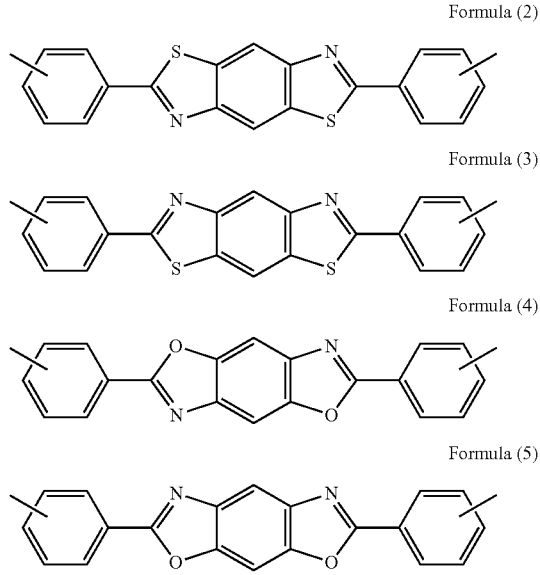

Formula (2)

Formula (3)

Formula (4)

Formula (5)

in which a hydrogen atom in the structures of the Formulae (2) to (5) may be substituted by a substituent; and the two groups of D each independently represent a group having a structure selected from the following structures:

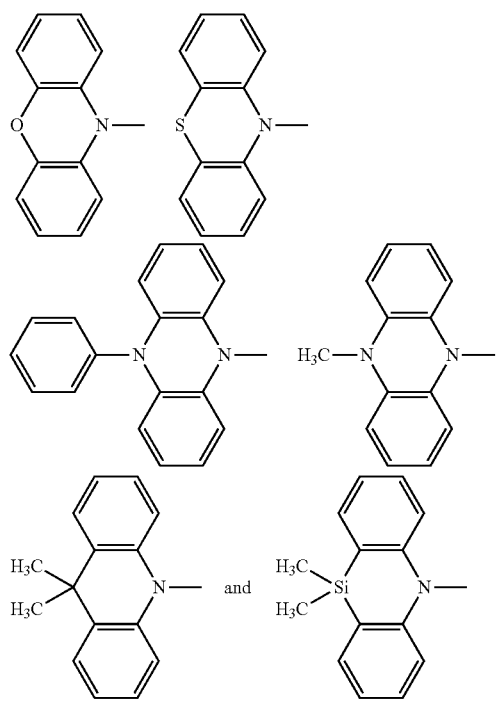

and in which a hydrogen atom in the above structures may be substituted by a substituent.

7. A delayed fluorescent emitter having a structure represented by the following Formula (1):

D-A-D          Formula (1)

82 wherein:

A represents a divalent group having a structure represented by one of the following Formulae (2) to (5):

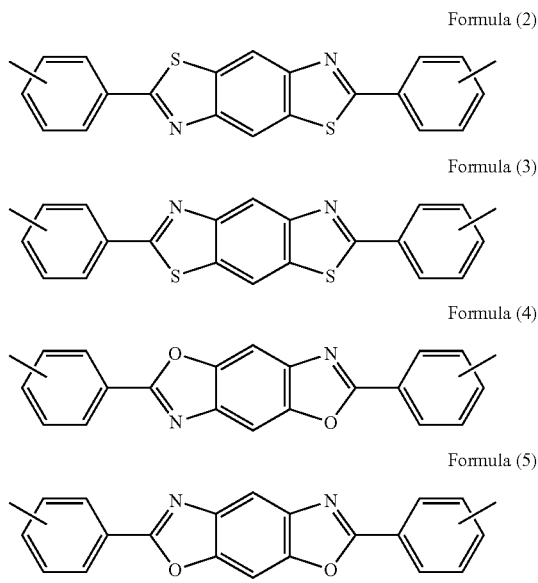

Formula (2)

Formula (3)

Formula (4)

Formula (5)

in which a hydrogen atom in the structures of the Formulae (2) to (5) may be substituted by a substituent; and the two groups of D each independently represent a group having a structure selected from the following structures:

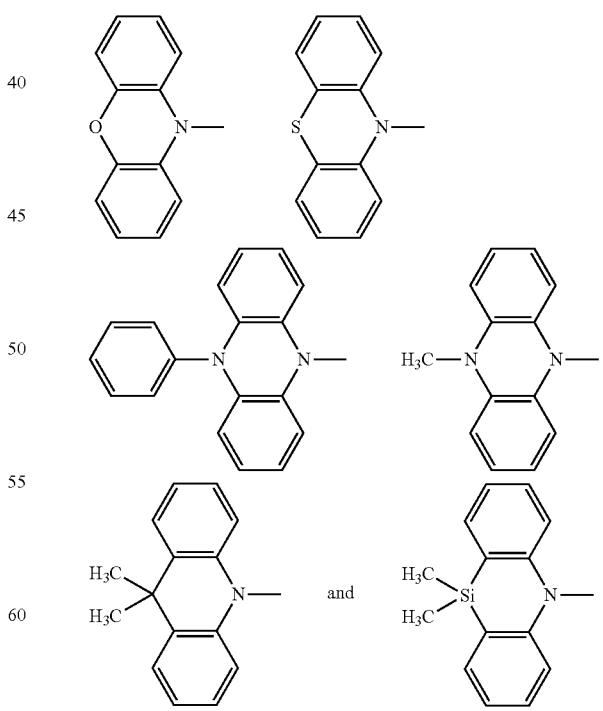

and in which a hydrogen atom in the above structures may be substituted by a substituent.

8. An organic light emitting device containing a substrate having thereon a light emitting layer containing a compound represented by the following Formula (1):

D-A-D      Formula (1)

wherein:

A represents a divalent group having a structure represented by one of the following Formulae (2) to (5):

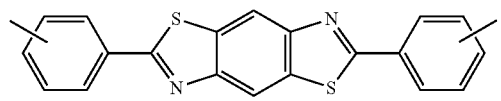

Formula (2)

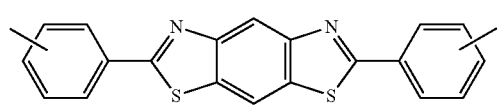

Formula (3)

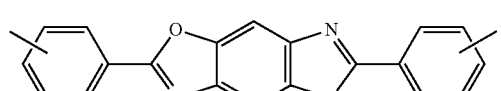

Formula (4)

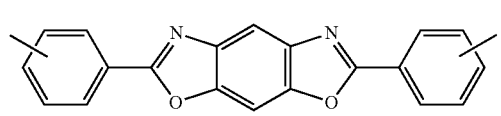

Formula (5)

in which a hydrogen atom in the structures of the formulae (2) to (5) may be substituted by a substituent; and the two groups of D each independently represent a group having a structure selected from the following structures:

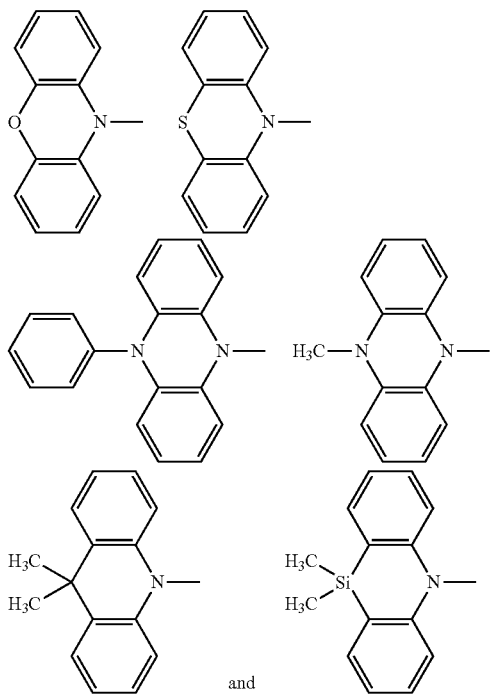

and in which a hydrogen atom in the above structures may be substituted by a substituent.

9. The organic light emitting device according to claim 8, wherein the organic light emitting device emits delayed fluorescent light.

10. The organic light emitting device according to claim 8, wherein the organic light emitting device is an organic electroluminescent device.

* * * * *